United States Patent
Basu et al.

(10) Patent No.: US 9,687,630 B2
(45) Date of Patent: Jun. 27, 2017

(54) METHODS AND COMPOSITIONS FOR TREATING POST-CARDIAL INFARCTION DAMAGE

(71) Applicant: Abbott Cardiovascular Systems, Inc., Santa Clara, CA (US)

(72) Inventors: Shubhayu Basu, Solon, OH (US); Gregory Waimong Chan, San Francisco, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 971 days.

(21) Appl. No.: 13/898,412

(22) Filed: May 20, 2013

(65) Prior Publication Data

US 2013/0338633 A1    Dec. 19, 2013

Related U.S. Application Data

(60) Continuation of application No. 12/963,397, filed on Dec. 8, 2010, now abandoned, and a division of
(Continued)

(51) Int. Cl.
*A61M 25/00* (2006.01)
*A61M 25/10* (2013.01)

(52) U.S. Cl.
CPC .......... *A61M 25/003* (2013.01); *A61M 25/00* (2013.01); *A61M 25/0084* (2013.01); *A61M 25/0032* (2013.01); *A61M 25/10* (2013.01)

(58) Field of Classification Search
CPC ................ A61M 5/321; A61M 5/3298; A61M 2005/3212; A61M 2025/0037;
(Continued)

(56) References Cited

U.S. PATENT DOCUMENTS

| | | | |
|---|---|---|---|
| 2,512,569 | A | 6/1950 | Saffir |
| 3,144,868 | A | 8/1964 | Jascalevich |

(Continued)

FOREIGN PATENT DOCUMENTS

| | | |
|---|---|---|
| EP | 0331584 | 9/1989 |
| EP | 0861632 | 9/1998 |

(Continued)

OTHER PUBLICATIONS

MSDA 4-amino-2,2,6,6-tetramethlypiperdine-1-oxyl (4-amino-TEMPO) CAS No. 14691-88-4 at www.chemcas.org/drug/analytical/cas*14691-88-4.asp (first published Sep. 2, 1997; revised Aug. 8, 2007; last visited Dec. 20, 2013). 5 pages.
(Continued)

*Primary Examiner* — Laura Bouchelle
*Assistant Examiner* — Justin L Zamory
(74) *Attorney, Agent, or Firm* — Randy Shen; Blakely, Sokoloff, Taylor & Zafman LLP

(57) ABSTRACT

Methods and compositions for treating post-myocardial infarction damage are herein disclosed. In some embodiments, a carrier with a treatment agent may be fabricated. The carrier can be formulated from a bioerodable, sustained-release substance. The resultant loaded carrier may then be suspended in at least one component of a two-component matrix system for simultaneous delivery to a post-myocardial infarction treatment area.

18 Claims, 12 Drawing Sheets

Related U.S. Application Data application No. 11/978,986, filed on Oct. 29, 2007, now abandoned, and a continuation-in-part of application No. 11/447,340, filed on Jun. 5, 2006, now Pat. No. 8,187,621, and a continuation-in-part of application No. 11/361,920, filed on Feb. 23, 2006, now Pat. No. 8,303,972, and a continuation-in-part of application No. 11/110,223, filed on Apr. 19, 2005, now Pat. No. 8,828,433.

(58) Field of Classification Search
CPC .. A61M 2025/0084; A61M 2025/0085; A61M 2025/0089; A61M 2025/0031; A61B 17/3494; A61B 17/3496; A61B 17/3474; A61B 17/3478; A61B 2017/00495
See application file for complete search history.

(56) References Cited

U.S. PATENT DOCUMENTS

| | | |
|---|---|---|
| 3,584,624 A | 6/1971 | de Ciutiis |
| 3,780,733 A | 12/1973 | Martinez-Manzor |
| 3,804,097 A | 4/1974 | Rudie |
| 3,890,976 A | 6/1975 | Bazell et al. |
| 4,141,973 A | 2/1979 | Balazs |
| 4,617,186 A | 10/1986 | Schafer et al. |
| 4,794,931 A | 1/1989 | Yock |
| 4,818,291 A | 4/1989 | Iwatsuki et al. |
| 4,842,590 A | 6/1989 | Tanabe et al. |
| 4,869,717 A | 9/1989 | Adair |
| 5,000,185 A | 3/1991 | Yock |
| 5,024,234 A | 6/1991 | Leary et al. |
| 5,026,350 A | 6/1991 | Tanaka et al. |
| 5,049,130 A | 9/1991 | Powell |
| 5,092,848 A | 3/1992 | DeCiutiis |
| 5,100,185 A | 3/1992 | Menke et al. |
| 5,109,859 A | 5/1992 | Jenkins |
| 5,116,317 A | 5/1992 | Carson et al. |
| 5,128,326 A | 7/1992 | Balazs et al. |
| 5,171,217 A | 12/1992 | March et al. |
| 5,202,745 A | 4/1993 | Sorin et al. |
| 5,203,338 A | 4/1993 | Jang |
| 5,242,427 A | 9/1993 | Bilweis |
| 5,270,300 A | 12/1993 | Hunziker |
| 5,291,267 A | 3/1994 | Sorin et al. |
| 5,306,250 A | 4/1994 | March et al. |
| 5,321,501 A | 6/1994 | Swanson et al. |
| 5,328,955 A | 7/1994 | Rhee et al. |
| 5,336,252 A | 8/1994 | Cohen |
| 5,354,279 A | 10/1994 | Hofling |
| 5,365,325 A | 11/1994 | Kumasaka et al. |
| 5,372,138 A | 12/1994 | Crowley et al. |
| 5,380,292 A | 1/1995 | Wilson |
| 5,419,777 A | 5/1995 | Hofling et al. |
| 5,437,632 A | 8/1995 | Engelson |
| 5,455,039 A | 10/1995 | Edelman et al. |
| 5,459,570 A | 10/1995 | Swanson et al. |
| 5,464,395 A | 11/1995 | Faxon et al. |
| 5,465,147 A | 11/1995 | Swanson |
| 5,485,486 A | 1/1996 | Gilhousen et al. |
| 5,499,630 A | 3/1996 | Hiki et al. |
| 5,516,532 A | 5/1996 | Atala et al. |
| 5,540,912 A | 7/1996 | Roorda et al. |
| 5,546,948 A | 8/1996 | Hamm et al. |
| 5,554,389 A | 9/1996 | Badylak et al. |
| 5,575,815 A | 11/1996 | Slepian et al. |
| 5,580,714 A | 12/1996 | Polovina |
| 5,580,856 A | 12/1996 | Prestrelski et al. |
| 5,588,432 A | 12/1996 | Crowley |
| 5,621,610 A | 4/1997 | Moore et al. |
| 5,631,011 A | 5/1997 | Wadstrom |
| 5,642,234 A | 6/1997 | Altman et al. |
| 5,655,548 A | 8/1997 | Nelson et al. |
| 5,667,778 A | 9/1997 | Atala |
| 5,669,883 A | 9/1997 | Scarfone et al. |
| 5,672,153 A | 9/1997 | Lax et al. |
| 5,676,151 A | 10/1997 | Yock |
| 5,693,029 A | 12/1997 | Leonhardt |
| 5,722,403 A | 3/1998 | McGee et al. |
| 5,725,551 A | 3/1998 | Myers et al. |
| 5,730,732 A | 3/1998 | Sardelis et al. |
| 5,740,808 A | 4/1998 | Panescu et al. |
| 5,749,915 A | 5/1998 | Slepian |
| 5,772,665 A | 6/1998 | Glad et al. |
| 5,785,689 A | 7/1998 | De Toledo et al. |
| 5,795,331 A | 8/1998 | Cragg et al. |
| 5,810,885 A | 9/1998 | Zinger |
| 5,811,533 A | 9/1998 | Gold et al. |
| 5,827,313 A | 10/1998 | Ream et al. |
| 5,843,156 A | 12/1998 | Slepian et al. |
| 5,874,500 A | 2/1999 | Rhee et al. |
| 5,879,713 A | 3/1999 | Roth et al. |
| 5,900,433 A | 5/1999 | Igo et al. |
| 5,906,934 A | 5/1999 | Grande et al. |
| 5,919,449 A | 7/1999 | Dinsmore |
| 5,935,160 A | 8/1999 | Auricchio et al. |
| 5,939,323 A | 8/1999 | Valentini et al. |
| 5,941,868 A | 8/1999 | Kaplan et al. |
| 5,957,941 A | 9/1999 | Ream |
| 5,968,064 A | 10/1999 | Selmon |
| 5,979,449 A | 11/1999 | Steer |
| 5,980,887 A | 11/1999 | Isner et al. |
| 5,981,568 A | 11/1999 | Kunz et al. |
| 5,984,908 A | 11/1999 | Davis et al. |
| 5,997,536 A | 12/1999 | Osswald et al. |
| 6,022,540 A | 2/2000 | Bruder et al. |
| 6,045,565 A | 4/2000 | Ellis et al. |
| 6,050,949 A | 4/2000 | White et al. |
| 6,051,071 A | 4/2000 | Charvet et al. |
| 6,051,648 A | 4/2000 | Rhee et al. |
| 6,056,744 A | 5/2000 | Edwards |
| 6,058,329 A | 5/2000 | Salo et al. |
| 6,060,053 A | 5/2000 | Atala |
| 6,068,599 A | 5/2000 | Saito et al. |
| 6,071,305 A | 6/2000 | Brown et al. |
| 6,086,582 A | 7/2000 | Altman et al. |
| 6,093,177 A | 7/2000 | Javier, Jr. et al. |
| 6,099,563 A | 8/2000 | Zhong |
| 6,099,864 A | 8/2000 | Morrison et al. |
| 6,102,887 A | 8/2000 | Altman |
| 6,102,904 A | 8/2000 | Vigil et al. |
| 6,102,926 A | 8/2000 | Tartaglia et al. |
| 6,120,520 A | 9/2000 | Saadat et al. |
| 6,120,904 A | 9/2000 | Hostettler et al. |
| 6,127,448 A | 10/2000 | Domb |
| 6,133,231 A | 10/2000 | Ferrara et al. |
| 6,134,003 A | 10/2000 | Tearney et al. |
| 6,146,373 A | 11/2000 | Cragg et al. |
| 6,151,525 A | 11/2000 | Soykan |
| 6,152,141 A | 11/2000 | Stevens et al. |
| 6,153,428 A | 11/2000 | Gustafsson et al. |
| 6,159,443 A | 12/2000 | Hallahan et al. |
| 6,162,202 A | 12/2000 | Sicurelli et al. |
| 6,175,669 B1 | 1/2001 | Colston et al. |
| 6,177,407 B1 | 1/2001 | Rodgers et al. |
| 6,179,809 B1 | 1/2001 | Khairkhahan et al. |
| 6,183,432 B1 | 2/2001 | Milo |
| 6,183,444 B1 | 2/2001 | Glines et al. |
| 6,187,330 B1 | 2/2001 | Wang et al. |
| 6,190,353 B1 | 2/2001 | Makower et al. |
| 6,191,144 B1 | 2/2001 | Isner |
| 6,192,271 B1 | 2/2001 | Hayman |
| 6,193,763 B1 | 2/2001 | Mackin |
| 6,197,324 B1 | 3/2001 | Crittenden |
| 6,201,608 B1 | 3/2001 | Mandella et al. |
| 6,206,893 B1 | 3/2001 | Klein et al. |
| 6,206,914 B1 | 3/2001 | Soykan et al. |
| 6,207,180 B1 | 3/2001 | Ottoboni et al. |
| 6,210,392 B1 | 4/2001 | Vigil et al. |
| 6,217,527 B1 | 4/2001 | Selmon et al. |
| 6,217,554 B1 | 4/2001 | Green |
| 6,221,049 B1 | 4/2001 | Selmon et al. |
| 6,231,546 B1 | 5/2001 | Milo et al. |
| 6,235,000 B1 | 5/2001 | Milo et al. |

(56) References Cited

U.S. PATENT DOCUMENTS

| | | |
|---|---|---|
| 6,241,710 B1 | 6/2001 | Van Tassel et al. |
| 6,251,104 B1 | 6/2001 | Kesten et al. |
| 6,283,947 B1 | 9/2001 | Mirzaee |
| 6,287,285 B1 | 9/2001 | Michal et al. |
| 6,290,729 B1 | 9/2001 | Slepian et al. |
| 6,296,602 B1 | 10/2001 | Headley |
| 6,299,604 B1 | 10/2001 | Ragheb et al. |
| 6,309,370 B1 | 10/2001 | Haim et al. |
| 6,312,725 B1 | 11/2001 | Wallace et al. |
| 6,315,994 B2 | 11/2001 | Usala et al. |
| 6,323,278 B2 | 11/2001 | Rhee et al. |
| RE37,463 E | 12/2001 | Altman |
| 6,328,229 B1 | 12/2001 | Duronio et al. |
| 6,331,309 B1 | 12/2001 | Jennings, Jr. et al. |
| 6,333,194 B1 | 12/2001 | Levy et al. |
| 6,334,872 B1 | 1/2002 | Termin et al. |
| 6,338,717 B1 | 1/2002 | Ouchi |
| 6,346,098 B1 | 2/2002 | Yock et al. |
| 6,346,099 B1 | 2/2002 | Altman |
| 6,346,515 B1 | 2/2002 | Pitaru et al. |
| 6,358,247 B1 | 3/2002 | Altman et al. |
| 6,358,258 B1 | 3/2002 | Arcia et al. |
| 6,360,129 B1 | 3/2002 | Ley et al. |
| 6,368,285 B1 | 4/2002 | Osadchy et al. |
| 6,371,935 B1 | 4/2002 | Macoviak et al. |
| 6,371,992 B1 | 4/2002 | Tanagho et al. |
| 6,379,379 B1 | 4/2002 | Wang |
| 6,385,476 B1 | 5/2002 | Osadchy et al. |
| 6,391,052 B2 | 5/2002 | Buirge et al. |
| 6,395,023 B1 | 5/2002 | Summers |
| 6,409,716 B1 | 6/2002 | Sahatjian et al. |
| 6,416,510 B1 | 7/2002 | Altman et al. |
| 6,425,887 B1 | 7/2002 | McGuckin et al. |
| 6,432,119 B1 | 8/2002 | Saadat |
| 6,436,135 B1 | 8/2002 | Goldfarb |
| 6,440,947 B1 | 8/2002 | Barron et al. |
| 6,443,941 B1 | 9/2002 | Slepian et al. |
| 6,443,949 B2 | 9/2002 | Altman |
| 6,447,504 B1 | 9/2002 | Ben-Haim et al. |
| 6,458,095 B1 | 10/2002 | Wirt et al. |
| 6,458,098 B1 | 10/2002 | Kanesaka |
| 6,464,862 B2 | 10/2002 | Bennett et al. |
| 6,465,001 B1 | 10/2002 | Hubbell et al. |
| 6,478,775 B1 | 11/2002 | Galt et al. |
| 6,478,776 B1 | 11/2002 | Rosenman et al. |
| 6,482,231 B1 | 11/2002 | Abatangelo et al. |
| 6,485,481 B1 | 11/2002 | Pfeiffer |
| 6,494,862 B1 | 12/2002 | Ray et al. |
| 6,514,217 B1 | 2/2003 | Selmon et al. |
| 6,544,227 B2 | 4/2003 | Sahatjian et al. |
| 6,544,230 B1 | 4/2003 | Flaherty et al. |
| 6,548,081 B2 | 4/2003 | Sadozai et al. |
| 6,554,801 B1 | 4/2003 | Steward et al. |
| 6,569,441 B2 | 5/2003 | Kunz et al. |
| 6,599,267 B1 | 7/2003 | Ray et al. |
| 6,602,241 B2 | 8/2003 | Makower et al. |
| 6,616,869 B2 | 9/2003 | Mathiowitz et al. |
| 6,620,927 B2 | 9/2003 | Bulpitt et al. |
| 6,624,245 B2 | 9/2003 | Wallace et al. |
| 6,628,988 B2 | 9/2003 | Kramer et al. |
| 6,629,947 B1 | 10/2003 | Sahatjian et al. |
| 6,632,457 B1 | 10/2003 | Sawhney |
| 6,635,267 B1 | 10/2003 | Miyoshi et al. |
| 6,660,034 B1 | 12/2003 | Mandrusov et al. |
| 6,663,881 B2 | 12/2003 | Kunz et al. |
| 6,682,730 B2 | 1/2004 | Mickel et al. |
| 6,689,608 B1 | 2/2004 | Mikos et al. |
| 6,692,466 B1 | 2/2004 | Chow et al. |
| 6,702,744 B2 | 3/2004 | Mandrusov et al. |
| 6,706,034 B1 | 3/2004 | Bhat |
| 6,726,677 B1 | 4/2004 | Flaherty et al. |
| 6,726,923 B2 | 4/2004 | Iyer et al. |
| 6,737,072 B1 | 5/2004 | Angele et al. |
| 6,748,258 B1 | 6/2004 | Mueller et al. |
| 6,749,617 B1 | 6/2004 | Palasis et al. |
| 6,759,431 B2 | 7/2004 | Hunter et al. |
| 6,761,887 B1 | 7/2004 | Kavalkovich et al. |
| 6,777,000 B2 | 8/2004 | Ni et al. |
| 6,777,231 B1 | 8/2004 | Katz et al. |
| 6,790,455 B2 | 9/2004 | Chu et al. |
| 6,824,791 B2 | 11/2004 | Mathiowitz et al. |
| 6,858,229 B1 | 2/2005 | Hubbell et al. |
| 6,916,488 B1 | 7/2005 | Meier et al. |
| 6,916,648 B2 | 7/2005 | Goddard et al. |
| 6,926,692 B2 | 8/2005 | Katoh et al. |
| 6,992,172 B1 | 1/2006 | Chang et al. |
| 7,008,411 B1 | 3/2006 | Mandrusov et al. |
| 7,035,092 B2 | 4/2006 | Hillman et al. |
| 7,112,587 B2 | 9/2006 | Timmer et al. |
| 7,129,210 B2 | 10/2006 | Lowinger et al. |
| 7,169,127 B2 | 1/2007 | Epstein et al. |
| 7,270,654 B2 | 9/2007 | Griego et al. |
| 7,273,469 B1 | 9/2007 | Chan et al. |
| 7,361,360 B2 | 4/2008 | Kitabwalla et al. |
| 7,374,774 B2 | 5/2008 | Bowlin et al. |
| 7,393,339 B2 | 7/2008 | Zawacki et al. |
| 7,438,692 B2 | 10/2008 | Tsonton et al. |
| 7,615,373 B2 | 11/2009 | Simpson et al. |
| 7,732,190 B2 | 6/2010 | Michal et al. |
| 7,815,590 B2 | 10/2010 | Cooper |
| 8,187,621 B2 | 5/2012 | Michal |
| 8,192,760 B2 | 6/2012 | Hossainy et al. |
| 8,303,972 B2 | 11/2012 | Michal |
| 8,741,326 B2 | 6/2014 | Michal |
| 8,828,433 B2 | 9/2014 | Claude |
| 9,005,672 B2 | 4/2015 | Michal |
| 2001/0023349 A1 | 9/2001 | Van Tassel et al. |
| 2001/0055615 A1 | 12/2001 | Wallace et al. |
| 2002/0006429 A1 | 1/2002 | Redmond et al. |
| 2002/0013408 A1 | 1/2002 | Rhee et al. |
| 2002/0042473 A1 | 4/2002 | Trollsas et al. |
| 2002/0072706 A1 | 6/2002 | Hiblar et al. |
| 2002/0076441 A1 | 6/2002 | Shih et al. |
| 2002/0077657 A1 | 6/2002 | Ginn et al. |
| 2002/0090725 A1 | 7/2002 | Simpson et al. |
| 2002/0102272 A1 | 8/2002 | Rosenthal et al. |
| 2002/0124855 A1 | 9/2002 | Chachques |
| 2002/0131974 A1 | 9/2002 | Segal |
| 2002/0142458 A1 | 10/2002 | Williams et al. |
| 2002/0146557 A1 | 10/2002 | Claude et al. |
| 2002/0151867 A1 | 10/2002 | McGuckin et al. |
| 2002/0169420 A1* | 11/2002 | Galt ............... A61B 17/00491 604/164.12 |
| 2002/0188170 A1 | 12/2002 | Santamore et al. |
| 2003/0023202 A1 | 1/2003 | Nielson |
| 2003/0040712 A1 | 2/2003 | Ray et al. |
| 2003/0050597 A1 | 3/2003 | Dodge et al. |
| 2003/0078671 A1 | 4/2003 | Lesniak et al. |
| 2003/0105493 A1 | 6/2003 | Salo |
| 2003/0114505 A1 | 6/2003 | Ueno et al. |
| 2003/0125766 A1 | 7/2003 | Ding |
| 2003/0175410 A1 | 9/2003 | Campbell et al. |
| 2003/0233150 A1 | 12/2003 | Bourne et al. |
| 2004/0002650 A1 | 1/2004 | Mandrusov et al. |
| 2004/0181206 A1 | 9/2004 | Chiu et al. |
| 2004/0185084 A1 | 9/2004 | Rhee et al. |
| 2004/0208845 A1 | 10/2004 | Michal et al. |
| 2004/0213756 A1 | 10/2004 | Michal et al. |
| 2004/0229856 A1 | 11/2004 | Chandrasekar et al. |
| 2005/0015048 A1 | 1/2005 | Chiu |
| 2005/0031874 A1 | 2/2005 | Michal et al. |
| 2005/0042254 A1 | 2/2005 | Freyman et al. |
| 2005/0064038 A1 | 3/2005 | Dinh et al. |
| 2005/0065281 A1 | 3/2005 | Lutolf et al. |
| 2005/0070844 A1 | 3/2005 | Chow et al. |
| 2005/0186240 A1 | 8/2005 | Ringeisen et al. |
| 2005/0281883 A1 | 12/2005 | Daniloff et al. |
| 2006/0069349 A1 | 3/2006 | Ganz |
| 2006/0149392 A1 | 7/2006 | Hsieh et al. |
| 2006/0233850 A1 | 10/2006 | Michal |
| 2006/0293612 A1* | 12/2006 | Jenson ............... A61B 17/3207 600/585 |
| 2007/0270948 A1 | 11/2007 | Wuh |

(56) References Cited

U.S. PATENT DOCUMENTS

| | | | |
|---|---|---|---|
| 2008/0025943 | A1 | 1/2008 | Michal et al. |
| 2012/0225040 | A1 | 9/2012 | Hossainy et al. |
| 2012/0225041 | A1 | 9/2012 | Hossainy et al. |

FOREIGN PATENT DOCUMENTS

| | | |
|---|---|---|
| EP | 0938871 | 9/1999 |
| EP | 1214077 | 1/2004 |
| FR | 2715855 | 8/1995 |
| GB | 2194144 | 3/1988 |
| JP | 61205446 | 9/1986 |
| JP | H02145600 | 6/1990 |
| JP | 06507106 | 8/1994 |
| JP | 10236984 | 9/1998 |
| JP | 3063935 | 12/1999 |
| JP | 2000502380 | 2/2000 |
| JP | 2000262525 | 9/2000 |
| JP | 2001-508754 | 7/2001 |
| JP | 2001508666 | 7/2001 |
| JP | 2003062089 | 3/2003 |
| JP | 2006014570 | 1/2006 |
| JP | 2006-516548 | 7/2006 |
| JP | 2007009185 | 1/2007 |
| JP | 2006523507 | 10/2009 |
| WO | WO-9210142 | 6/1992 |
| WO | WO-9315781 | 8/1993 |
| WO | WO-9522316 | 8/1995 |
| WO | WO-9830207 | 7/1998 |
| WO | WO-9854301 | 12/1998 |
| WO | WO-9953943 | 10/1999 |
| WO | WO-0016818 | 3/2000 |
| WO | WO-0054661 | 9/2000 |
| WO | WO-0071196 | 11/2000 |
| WO | WO-0124775 | 4/2001 |
| WO | WO-0124842 | 4/2001 |
| WO | WO-0145548 | 6/2001 |
| WO | WO-0149357 | 7/2001 |
| WO | WO-0200173 | 1/2002 |
| WO | WO-0204008 | 1/2002 |
| WO | WO-0228450 | 4/2002 |
| WO | WO-0240070 | 5/2002 |
| WO | WO-02072166 | 9/2002 |
| WO | WO-02087623 | 11/2002 |
| WO | WO-03005961 | 1/2003 |
| WO | WO-03022324 | 3/2003 |
| WO | WO-03022909 | 3/2003 |
| WO | WO-03026492 | 4/2003 |
| WO | WO-03027234 | 4/2003 |
| WO | WO-03064637 | 8/2003 |
| WO | WO-04000915 | 12/2003 |
| WO | WO-2004050013 | 6/2004 |
| WO | WO-2004058305 | 7/2004 |
| WO | WO-2004060346 | 7/2004 |
| WO | WO-2004066829 | 8/2004 |
| WO | WO-2004091592 | 10/2004 |
| WO | WO-2004098669 | 11/2004 |
| WO | WO-2005061019 | 7/2005 |
| WO | WO-2005067890 | 7/2005 |
| WO | WO-2006014570 | 2/2006 |
| WO | WO-2006027549 | 3/2006 |
| WO | WO-2006039072 | 4/2006 |
| WO | WO-2006113407 | 10/2006 |
| WO | WO-2007048831 | 3/2007 |
| WO | WO-2007145909 | 12/2007 |

OTHER PUBLICATIONS

Abbott Cardiovascular Systems, Office Action dated Apr. 6, 2009 for U.S. Appl. No. 11/447,340.
Abbott Cardiovascular Systems, Office Action dated Mar. 30, 2009 for U.S. Appl. No. 10/792,960,
Abbott Cardiovascular Systems, Office Action dated Apr. 13, 2009 for U.S. Appl. No. 11/566,643.
Abbott Cardiovascular Systems, Office Action dated May 12, 2009 for U.S. Appl. No. 11/496,824.
Abbott Cardiovascular Systems, Non-Final Office Action dated Mar. 5, 2009 for U.S. Appl. No. 11/507,860.
Abbott Cardiovascular Systems, Non-Final Office Action dated Mar. 13, 2009 for U.S. Appl. No. 10/414,602.
Abbott Cardiovascular Systems, International search report and written opinion dated Jun. 18, 2009 for PCT/US2008/051505.
Abbott Cardiovascular Systems, Non final office action dated Jul. 9, 2009 for U.S. Appl. No. 11/561,328.
Abbott Cardiovascular Systems, Non final office action dated Aug. 5, 2009 for U.S. Appl. No. 11/031,608.
Abbott Cardiovascular Systems, International Preliminary Report on Patentability dated Jul. 30, 2009 for PCT/US2008/051505.
Abbott Cardiovascular Systems, Final office action dated Nov. 12, 2009 for U.S. Appl. No. 12/013,286.
Abbott Cardiovascular Systems, Final office action dated Nov. 25, 2009 for U.S. Appl. No. 11/566,643.
Abbott Cardiovascular Systems, Non final office action dated Dec. 9, 2009 for U.S. Appl. No. 10/781,984.
Abbott Cardiovascular Systems, Examination Report dated Jan. 13, 2010 for EP Application No. 07795729.8.
Abbott Cardiovascular Systems, Non final office action dated Feb. 5, 2010 for U.S. Appl. No. 11/447,340.
Abbott Cardiovascular Systems, Final Office Action dated Jan. 29, 2010 for U.S. Appl. No. 10/792,960.
Abbott Cardiovascular Systems, Examination Report dated Jan. 15, 2010 for EP 08727952.7.
Abbott Cardiovascular Systems, Examination Report dated Feb. 5, 2010 for EP 07810637.4.
Abbott Cardiovascular Systems, Final office action dated Mar. 29, 2010 for U.S. Appl. No. 11/031,608.
Abbott Cardiovascular Systems, Non final office action dated Apr. 29, 2010 for U.S. Appl. No. 10/792,960.
Abbott Cardiovascular Systems, Non-Final Office Action dated Jun. 4, 2010 for U.S. Appl. No. 10/781,984.
Abbott Cardiovascular Systems, Final Office Action dated Jun. 11, 2010 for U.S. Appl. No. 11/561,328.
Abbott Cardiovascular Systems, Final Office Action mailed Jul. 15, 2010, U.S. Appl. No. 11/507,860, 10 pages., 10 pages.
Abbott Cardiovascular Systems, Non final office action dated Aug. 13, 2010 for U.S. Appl. No. 11/447,340.
Abbott Cardiovascular Systems, Final office action mailed Sep. 27, 2010 for U.S. Appl. No. 10/792,960.
Abbott Cardiovascular Systems, Final office action mailed Sep. 27, 2010 for U.S. Appl. No. 12/016,180.
Abbott Cardiovascular Systems, Final Office Action mailed Nov. 22, 2010 for U.S. Appl. No. 10/781,984, 13 pages.
Abbott Cardiovascular Systems, Non-final Office Action mailed Nov. 24, 2010 for U.S. Appl. No. 12/013,286, 11 pages.
Abbott Cardiovascular Systems, Non-final Office Action mailed Dec. 8, 2010 for U.S. Appl. No. 11/566,643, 17 pages.
Abbott Cardiovascular Systems, Non-final Office Action mailed Dec. 10, 2010 for U.S. Appl. No. 11/938,782, 32 pages.
Abbott Cardiovascular Systems, Non-final Office Action mailed Dec. 17, 2010 for U.S. Appl. No. 11/933,922, 23 pages.
Abbott Cardiovascular Systems, website for Healon (R) OVD, copyright 2010, accessed Dec. 15, 2010, URL: <http://abbottmedicaloptics.com/products/cataract/ovds/healon-viscoelastic>, (2010), 2 pages.
Abbott Cardiovascular Systems, Product Information Sheet for Healon (R), from Abbott Medical Optics, (2005), 1 page.
Abbott Cardiovascular Systems, Office Action dated Apr. 29, 2009 for U.S. Appl. No. 12/013,286.
Abbott Cardiovascular Systems, Non final office action dated Apr. 14, 2010 for U.S. Appl. No. 12/016,180.
Abbott Cardiovascular Systems, Final office action dated Apr. 22, 2010 for U.S. Appl. No. 10/414,602.
Abbott Cardiovascular Systems, Japanese Office Action dated Dec. 8, 2010 for Japanese Patent App No. 2006-509975., 6 pages.
Abbott Cardiovascular Systems, Non final office action mailed Feb. 8, 2011 for U.S. Appl. No. 10/792,960.

(56) References Cited

OTHER PUBLICATIONS

Abbott Cardiovascular Systems, Final Office Action mailed Apr. 15, 2011 for U.S. Appl. No. 10/414,602.
Abbott Cardiovascular Systems, Non final office action mailed Nov. 8, 2011 for U.S. Appl. No. 10/792,960.
Abbott Cardiovascular Systems, Final Office Action mailed Dec. 13, 2011 for U.S. Appl. No. 12/963,397, 15 pages.
Abbott Cardiovascular Systems, Final Office Action mailed Jan. 5, 2012 for U.S. Appl. No. 11/361,920, 13 pages.
Abbott Cardiovascular Systems, Office Action mailed Jan. 17, 2012 for European Patent Application 08727952.7, 6 pages.
Abbott Cardiovascular Systems, Non-Final Office Action mailed Jan. 30, 2012 for U.S. Appl. No. 10/781,984, 10 pages.
Abbott Cardiovascular Systems, Final Office Action mailed mailed Feb. 8, 2012 for Japanese application No. 2006-509975, 6 pages.
Abbott Cardiovascular Systems, Non-Final Office Action mailed Feb. 15, 2012 for U.S. Appl. No. 12/114,717, 16 pages.
Abbott Cardiovascular Systems, Final Office Action mailed Apr. 4, 2012 for U.S. Appl. No. 10/792,960, 13 pages.
Abbott Cardiovascular Systems, European Office Action mailed Apr. 11, 2012 for App No. 12155231.9, 9 pages.
Abbott Cardiovascular Systems, European Office Action mailed Apr. 10, 2012 for App No. 07810637.4, 6 pages.
Abbott Cardiovascular Systems, Final Office Action mailed May 9, 2012 for U.S. Appl. No. 11/110,223., 12 pages.
Abbott Cardiovascular Systems, European Search report for application No. 12151788.2 mailed Apr. 18, 2012, 6 pages.
Abbott Cardiovascular Systems, Non-final Office Action mailed Jun. 22, 2012 for U.S. Appl. No. 12/963,397, 10 pages.
Abbott Cardiovascular Systems, Restriction requirement mailed Jul. 3, 2012 for U.S. Appl. No. 13/472,324, 8 pages.
Abbott Cardiovascular Systems, Non-final Office Action mailed Jun. 26, 2012 for U.S. Appl. No. 12/632,612., 8 pages.
Abbott Cardiovascular Systems, Japanese Office Action dated Jun. 11, 2012 for Appln. No. 2010-162711.
Abbott Cardiovascular Systems, Non-final Office Action mailed Aug. 28, 2012 for U.S. Appl. No. 13/472,324.
Abbott Cardiovascular Systems, Non-final Office Action mailed Aug. 30, 2012 for U.S. Appl. No. 13/472,328.
Abbott Cardiovascular Systems, Non-Final Office Action Sep. 11, 2012 for U.S. Appl. No. 10/792,960.
Abbott Cardiovascular Systems, Japanese office action dated Aug. 20, 2012 for JP 2009-537153.
Abbott Cardiovascular Systems, Non-Final Office Action dated Oct. 3, 2012 for U.S. Appl. No. 12/756,119.
Abbott Cardiovascular Systems, Non final office action mailed Jun. 7, 2011 for U.S. Appl. No. 11/447,340.
Abbott Cardiovascular Systems, Non final office action mailed Jul. 6, 2011 for U.S. Appl. No. 10/781,984.
Abbott Cardiovascular Systems, Final office action mailed Jun. 28, 2011 for U.S. Appl. No. 10/792,960.
Abbott Cardiovascular Systems, Final office action mailed Jul. 18, 2011 for U.S. Appl. No. 11/566,643.
Abbott Cardiovascular Systems, Non-Final Office Action mailed Aug. 31, 2011 for U.S. Appl. No. 11/110,223, 11 pages.
Abbott Cardiovascular Systems, Final office action mailed Sep. 20, 2011 for U.S. Appl. No. 11/938,752.
Abbott Cardiovascular Systems, Final Office Action mailed Oct. 21, 2011 for U.S. Appl. No. 10/781,984, 10 pages.
Abbott Cardiovascular Systems, et al., Japanese Office Action dated Aug. 27, 2012 for JP 2009-522776.
Abbott Cardiovascular Systems, Final Office Action dated Nov. 8, 2012 for U.S. Appl. No. 12/114,717.
Abbott Cardiovascular Systems, Final Office Action mailed Nov. 7, 2012 for U.S. Appl. No. 10/781,984.
Abbott Cardiovascular Systems, Japanese Office Action dated Nov. 19, 2012 for Appln. No. 2009-539265.
Abbott Cardiovascular Systems, Final office action dated Jan. 18, 2013 for U.S. Appl. No. 12/963,397.
Abbott Cardiovascular Systems, Japanese office action dated Oct. 9, 2012 for JP Appln. No. 2009-514330.
Abbott Cardiovascular Systems, Japanese Office Action mailed Dec. 17, 2012 for JP Appln. No. 2009-546553.
Abbott Cardiovascular Systems, Examination Report dated Feb. 20, 2013 for European Appln. No. 12151788.2, 4 pages.
Abbott Cardiovascular Systems, Non final office action dated Apr. 1, 2013 for U.S. Appl. No. 13/559,423.
Abbott Cardiovascular Systems, Non-Final Office Action dated Oct. 3, 2012 for U.S. Appl. No. 12/756,092.
Abbott Cardiovascular Systems, Japanese office action mailed Mar. 25, 2013 for JP 2009-539265.
Abbott Cardiovascular Systems in, PCT Search Report and Written Opinion dated Aug. 26, 2008 for PCT/US2007/016433.
Abbott Cardiovascular Systems in, PCT Search Report and Written Opinion dated Jul. 31, 2008 for PCT/US2007/024158.
Abbott Cardiovascular Systems in, PCT International Preliminary Report on Patentability and Written Opinion dated Dec. 24, 2008 for PCT/US2007/013181.
Abbott Cardiovascular Systems in, "PCT International Search Report and Written Opinion mailed Feb. 10, 2009", PCT/US2007/023419.
Abbott Cardiovascular Systems in, "PCT Search Report dated Feb. 12, 2008", PCT Appln No. PCT/US2007/013181, 17.
Abbott Cardiovascular Systems in, "PCT Search Report dated Jan. 31, 2007", PCT Appln No. PCT/US2006/014021, 11.
Abbott Cardiovascular Systems in, "PCT Search Report dated Mar. 27, 2008", PCT Appln No. PCT/US2007/003614, 18.
Advanced Cardiovascular Systems, Extended European search report dated Apr. 21, 2011 for EP Application No. 10186186.2.
Advanced Cardiovascular Systems, Extended EP Search Report dated May 20, 2011 for EP Application No. 10186197.9.
Advanced Cardiovascular Systems, Inc. , et al., "PCT International Preliminary Report on Patentability dated Jun. 19, 2007", PCT Appln. No. PCT/US2005/045627.
Advanced Cardiovascular Systems, Inc. , "PCT International Preliminary Report on Patentability dated Nov. 3, 2005", PCT Appln. No. PCT/US2004/011356, 6 pages.
Advanced Cardiovascular Systems, Inc. , "PCT International Search Report and Written Opinion mailed Oct. 13, 2006", PCT Appln No. PCT/US2005/045627.
Advanced Cardiovascular Systems, Inc. , "PCT International Search Report dated Feb. 9, 2004", PCT Appln. No. PCT/US03/30464, 5 pages.
Advanced Cardiovascular Systems, Inc. , "PCT International Search Report dated Jan. 28, 2004", PCT Appln. No. PCT/US03/18360, 7 pages.
Advanced Cardiovascular Systems, Inc. , "PCT Invitation to Pay Additional Fees mailed Nov. 4, 2003", PCT Appln No. PCT/US03/18360, 3 pages.
Advanced Cardiovascular Systems, Inc. , "PCT Search Report and Written Opinion dated Nov. 24, 2004", PCT Appln. No. PCT/US2004/011356, 12 pages.
Agocha, A. , et al., "Hypoxia regulates basal and induced DNA synthesis and collagen type I production in human cardiac fibroblasts: effects of transforming growth factor-beta 1, thyroid hormone, angiotensin II and basic fibroblast growth factor", *J. Mol. Cell. Cardiol.*, 29(8), (Apr. 1997), pp. 2233-2244.
Allemann, E. , et al., "Kinetics of Blood Component Adsorption on poly(D,L-lactic acid) Nanoparticles: Evidence of Complement C3 Component Involvement", *J. Biomed. Mater. Res.*, 37(2), Abstract downloaded from the Internet at www.ncbi.nlm.nih.gov/entrez/query.fcgi?cmd=Retrieve&db=PubMed, (Nov. 1997), 229-234.
Anderson, James M., et al., "Biodegradation and biocompatibility of PLA and PLGA microspheres", *Advanced Drug Deliver Reviews 28*, (1997), 5-24.
Assmus, B. , et al., "Transplantation of Progenitor Cells and Regeneration Enhancement in Acute Myocardial Infarction (TOPCARE-AMI)", *Clinical Investigation and Reports*, Circulation, 106, (2002), 3009-3017.
Baxter Healthcare Corporation, "FloSeal Matrix Hemostatic Sealant", fusionmed.com/docs/surgeon/default.asp, (2002), pp. 1-2.

(56) References Cited

OTHER PUBLICATIONS

Berger, et al., "Poly-L-cysteine", *J. Am. Chem. Soc.*, 78(17), (Sep. 5, 1956), pp. 4483-4488.
Bernatowicz, M., et al., "Preparation of Boc-[S-(3-nitro-2-pyridinesulfenyl)]-cysteine and its use for Unsymmetrical Disulfide Bond Formation", *Int. J. Peptide Protein Res.* 28(2), (Aug. 1996), pp. 107-112.
Boland, E. D., "Electrospinning Collagen and Elastin: Preliminary Vascular Tissue Engineering", *Frontiers in Bioscience*, vol. 9, (May 1, 2004), pp. 1422-1432.
Brust, G., "Polyimides", *Department of Polymer Science; The University of Southern Mississippi*, pslc.usm.edu/macrog/imide.htm, (2005), pp. 1-4.
Bull, S., et al., "Self-Assembled Peptide Amphiphile Nanofibers Conjugated to MRI Contrast Agents", *Nano Letters*, vol. 5, No. 1, (Jan. 2005), 4 pages.
Buschmann, I, et al., "Arteriogenesis versus angiogenesis: Two mechanisms of vessel growth", *News Physiol. Sci.*, vol. 14 (Jun. 1999), 121-125.
Canderm Pharma, "Technical Dossier: Artecoll", downloaded from the Internet on Oct. 22, 2002 from: http://www.canderm.com/artecoll/tech.html, pp. 1-3.
Capan, Y., et al., "Preparation and Characterization of Poly(D,L-lactide-co-glycolide) Microspheres for Controlled Release of Human Growth Hormone", *AAPS PharmSciTech.*, 4(2) Article 28, (2003), 1-10.
Caplan, Michael J., et al., "Dependence on pH of polarized sorting of secreted proteins", *Nature*, vol. 29, (Oct. 15, 1987), 630.
Carpino, L., et al., "Tris(2-aminoethyl)amine as a Substitute for 4-(Aminomethyl)piperidine in the FMOC/Polyamine Approach to Rapid Peptide Synthesis", *J. Org. Chem.*, 55(5), (Mar. 1990), pp. 1673-1675.
Chandy, et al., "The development of porous alginate/elastin/PEG composite matrix for cardiovascular engineering", *Journal of Biomaterials Applications*, vol. 17, (Apr. 2003), 287-301.
Choi, Young Seon, et al., "Study on gelatin-containing artificial skin: I. Preparation and characteristics of novel gelatin-alginate sponge", *Biomaterials*, vol. 20, (1999), 409-417.
Chung, Y., et al., "Sol-gel transition temperature of PLGA-g-PEG aqueous solutions", *Biomacromolecules*, vol. 3, No. 3, (May 2002), 511-516.
Corbett, S., et al., "Covalent Cross-linking of Fibronectin to Fibrin is Required for Maximal Cell Adhesion to a Fibronectin-Fibrin Matrix", *The Journal of Biological Chemistry*, 272(40), (Oct. 3, 1997), pp. 24999-25005.
Creemers, E., et al., "Matrix Metalloproteinase Inhibition After Myocardial Infarction: A New Approach to Prevent Heart Failure?", *Circ. Res.*, vol. 89, (2001), pp. 201-210.
Crivello, et al., "Synthesis and Photoinitiated Cationic Polymerization of Monomers with the Silsesquioxane Core", *J Polym Science: Part A: Polymer Chemistry* 35, (1997), pp. 407-425.
Csonka, E., et al., "Interspecific Interaction of Aortic Endothelial and Smooth Muscle Cells", *Acta Morphologica Hungarica*, vol. 35, No. 1-2, (1987), 31-35.
Davis, M. E., et al., "Injectable Self-Assembling Peptide Nanofibers Create Intramyocardial Microenvironments for Endothelial Cells", *Circulation*, 111, (Feb. 2005), pp. 442-450.
Davis, M E., et al., "Injectable Self-Assembling Peptide Nanofibers Create Intramyocardial Microenvironments for Endothelial Cells", *Circulation*, 111, (2005), 442-450.
De Rosa, et al., "Biodegradable Microparticles for the Controlled Delivery of Oligonucleotides", *International Journal of Pharmaceutics*, 242, (Aug. 21, 2002), pp. 225-228.
Desai, M., et al., "Polymer bound EDC (P-EDC): A convenient reagent for formation of an amide bond", *Tetrahedron Letters*, 34(48), Abstract downloaded from the Internet at sciencedirect.com, (Nov. 1993), 7685-7688.
Dinbergs, et al., "Cellular response to transforming growth factor-β1 and basic fibroblast growth factor depends on release kinetics and extracellular matrix interactions", *The Journal of Biological Chemistry*, vol. 271, No. 47, (Nov. 1996), 29822-29829.
Dong, Zhanfeng, et al., "Alginate/gelatin blend films and their properties for drug controlled release", *Journal of Membrane Science*, vol. 280, (2006), 37-44.
Edelman, "Controlled and modulated release of basic fibroblast growth factor", *Biomaterials*, vol. 12, (Sep. 1999), 619-626.
Elbert, D. L., et al., "Protein delivery from materials formed by self-selective conjugate addition reactions", *Journal of Controlled Release*, 76, (2001), 11-25.
Etzion, S., et al., "Influence of Embryonic Cardiomyocyte Transplantation on the Progression of Heart Failure in a Rat Model of Extensive Myocardial Infarction", *J. Mol. Cell Cardiol.*, 33, (May 2001), pp. 1321-1330.
Ferrara, N., "Role of Vascular Endothelial Growth Factor in the Regulation of Angiogenesis", *Kidney International*, 56(3), Abstract downloaded from the Internet at nature.com/ki/journal/v56/n3/abs/4490967a.html, (1999), 794-814.
Friedman, Paul M., et al., "Safety Data of Injectable Nonanimal Stabilized Hyaluronic Acid Gel for Soft Tissue Augmentation", *Dermatologic Surgery*, vol. 28, (2002), pp. 491-494.
Fuchs, S., et al., "Catheter-Based Autologous Bone Marrow Myocardial Injection in No-Option Patients with Advanced Coronary Artery Disease", *J. Am. Coll. Cardiol.*, 41(10), (2003), pp. 1721-1724.
Fukumoto, S., et al., "Protein Kinase C δ Inhibits the Proliferation of Vascular Smooth Muscle Cells by Suppressing G1 Cyclin Expression", *The Journal of Biological Chemistry*, 272(21), (May 1997), pp. 13816-13822.
Giordano, F., et al., "Angiogenesis: The Role of the Microenvironment in Flipping the Switch", *Current Opinion in Genetics and Development*, 11, (2001), pp. 35-40.
Gossler, et al., "Transgenesis by means of blastocyst-derived embryonic stem cell lines", *Proc. Natl. Acad. Sci. USA*, 83, (Dec. 1986), pp. 9065-9069.
Grafe, T. H., "Nanofiber Webs from Electrospinning", *Presented at the Nonwovens in Filtration—Fifth International Conference,*, Stuttgart, Germany, (Mar. 2003), pp. 1-5.
Gref, R., et al., "Biodegradable Long-Circulating Polymeric Nanospheres", *Science*, 263(5153), Abstract downloaded from the Internet at: http://www.sciencemag.org/cgi/content/abstract/263/5153/1600, 1 page, (Mar. 1994).
Griese, D. P., et al., "Vascular gene delivery of anticoagulants by transplantation of retrovirally-transduced endothelial progenitor cells", *Cardiovascular Research*, vol. 58, (2003), 469-477.
Grund, F., et al., "Microembolization in Pigs: Effects on Coronary Blood Flow and Myocardial Ischemic Tolerance", *Am. J. Physiol.*, 277 (Heart Circ. Physiol. 46), (1999), pp. H533-H542.
Gupta, et al., "Changes in Passive Mechanical Stiffness of Myocardial Tissue with Aneurysm Formation", *Circulation*, 89(5), (May 1994), pp. 2315-2326.
Hanawa, T., et al., "New oral dosage form for elderly patients: preparation and characterization of silk fibroin gel", *Chemical and Pharmaceutical Bulletin, Pharmaceutical Society of Japan*, Tokyo, vol. 43, No. 2, (Jan. 1995), 284-288.
Hao, X, et al., "Angiogenic Effects of Sequential release of VEGF-A 165 and PDGF-BB with Alginate Hydrogels After Myocardial Infarction", *Cardiovascular Research*, 75(1), (Apr. 6, 2007), 178-185.
Hao, X, et al., "Angiogenic effects of sequential release of VEGF-A165 and PDGF-BB with alginate hydrogels after myocardial infarction", *Cardiovascular Research*, 75, (2007), 178-185.
Hartgerink, J. D., et al., "Peptide-amphiphile nanofibers: A versatile scaffold for the preparation of self-assembling materials", *PNAS*, vol. 99, No. 8, (Apr. 16, 2002), 5133-5138.
Hartgerink, J. D., et al., "Self-Assembly and Mineralization of Peptide-Amphiphile Nanofibers", *Science*, vol. 294, (Nov. 23, 2001), 1684-1688.
Hashimoto, T., et al., "Development of Alginate Wound Dressings Linked with Hybrid Peptides Derived from Laminin and Elastin", *Biomaterials*, 25, (2004), pp. 1407-1414.

(56) References Cited

OTHER PUBLICATIONS

Haugland, et al., "Dialkylcarbocyanine and Dialkylaminostryryl Probes", *Handbook of Fluorescent Probes and Research Products*, Molecular Probes Inc., (2002), 530-534.

Haugland, et al., "Membrane-permeant reactive tracers", *Handbook of Fluorescent Probes and Research Products*, Molecular Probes, Inc., (2002), 458-553.

Haynesworth, Stephen E., et al., "Platelet Effects on Human Mesenchymal Stem Cells", Abstract, presented at *Orthopaedic Research Society 48th Annual Meeting*, Dallas, TX, (Feb. 10-13, 2010), 2 pages.

Heeschen, C., et al., "Nicotine Stimulates Tumor Angiogenesis", *American College of Cardiology*, 37(2) Supplement A,, Abstract downloaded from the Internet at: http://24.132.160.238/ciw-01acc/abstract_search_author.cfm?SearchName=Heeschen, 1 page, (Feb. 2001), pp. 1A-648A.

Helisch, A, et al., "Angiogenesis and arteriogenesis", *NEUE Diagnostische Und Therap. Verfahren, Z Kardiol 89*, (2000), 239-244.

Hendel, R. C., et al., "Effect of Intracoronary Recombinant Human Vascular Endothelial Growth Factor on Myocardial Perfusion: Evidence for a Dose-Dependent Effect", *Cirulation*, 101, (2000), pp. 118-121.

Henry, R. R., et al., "Insulin Action and Glucose Metabolism in Nondiabetic Control and NIDDM Subjects: Comparison Using Human Skeletal Muscle Cell Cultures", *Diabetes*, 44(8), Abstract downloaded from the Internet at www.diabetes.diabetesjournals.org/cgi/content/abstract/44/8/936, (1995), pp. 936-946.

Hoffman, "Hydrogels for Biomedical Applications", *Advanced Drug Delivery Reviews*, vol. 43, (2002), pp. 3-12.

Holland, N. B., et al., "Biomimetic Engineering of Non-Adhesive glycocalyx-like Surfaces Using Oligosaccharide Surfactant Polymers", *Nature*, 392, Abstract downloaded from the Internet at www.nature.com, (Apr. 1998), pp. 799-801.

Horan, R.L., et al., "In Vitro Degradation of Silk Fibroin", *Biomaterials*, vol. 26, (2004), 3385-3393.

Hovinen, J., et al., "Synthesis of 3'-functionalized oligonucleotides on a single solid support", *Tetrahedron Letters*, 34(50), Abstract downloaded from the Internet at www.sciencedirect.com, (Dec. 1993), pp. 8169-8172.

Huang, K., et al., "Synthesis and Characterization of Self-Assembling Block Copolymers Containing Bioadhesive End Groups", *Biomacromolecules*, 3(2), (2002), pp. 397-406.

Hutcheson, K., et al., "Comparison of Benefits on Myocardial Performance of Cellular Cardiomyoplasty with Skeletal Myoblasts and Fibroblasts", *Cell Transplantation*, 9(3), (2000), pp. 359-368.

Huynh, T. V., et al., "Constructing and Screening cDNA Libraries in λgt10 and λgt11", *Chapter 2 in DNA Cloning, vol. 1: A Practical Approach*, ed. by D.M. Glover, (1985), pp. 49-78.

Indik, Z., et al., "Production of Recombinant Human Tropoelastin: Characterization and Demonstration of Immunologic and Chemotactic Activity", *Arch. Biochem. Biophys.*, 280(1), Abstract downloaded from the Internet at: http://www.ncbi.nlm.nih.gov/entrez/query.fcgi?cmd=Retrieve&db=PubMed, 1 page (Jul. 1990), pp. 80-86.

Iskandrian, A. S., et al., "Nuclear Cardiac Imaging: Principles and Applications", second edition, *F.A. Davis Co.*, Philadelphia, cover page, title page and TOC, (1996), 5 pages total.

Isner, J. M., "Vascular Endothelial Growth Factor: Gene Therapy and Therapeutic Angiogenesis", *Am. J. Cardiol.*, 82(10A), (Nov. 19, 1998), pp. 63S-64S.

Ito, Wulf D., et al., "Monocyte chemotactic protein-1 increases collateral and peripheral conductance after femoral artery occlusion", *Max-Planck-Institute for Physiological and Clinical Research*, Bad Nauheim, Germany, (Feb. 21, 1997), pp. 829-837.

Johnson, et al., "The stabilization and encapsulation of human growth hormone nto biodegradable microspheres", *Pharmaceutical Research*, vol. 14, No. 6, (1997), 730-735.

Jonasson, P., et al., "Denatured states of human carbonic anhydrase II: an NMR study of hydrogen/deuterium exchange at tryptophan-indole-Hn sites", *FEBS Letters*, 445, (1999), pp. 361-365.

Kalltorp, Mia, et al., "Inflammatory cell recruitment, distribution, and chemiluminescence response at IgG precoated- and thiol functionalized gold surfaces", *Swedish Biomaterials Consortium, Swedish Foundation for Strategic Research*, (Apr. 9, 1999), 251-259.

Kaplan, D.L., et al., "Spiderless Spider Webs", *Nature Biotechnology*, vol. 20, (2002), 239-240.

Kawai, et al., "Accelerated tissue regeneration through incorporation of basic fibroblast growth factor-impregnated gelatin microspheres into artificial dermis", *Biomaterials*, 21(5), (Mar. 2000), 489-499.

Kawasuji, M., et al., "Therapeutic Angiogenesis with Intramyocardial Administration of Basic Fibroblast Growth Factor", *Ann Thorac Surg*, 69, Abstract downloaded from the Internet at www.ats.ctsnetjournals.org/cgi/content/abstract/69/4/1155, (2000), pp. 1155-1161.

Kelley, et al., "Restraining Infarct Expansion Preserves Left Ventricular Geometry and Function After Acute Anteroapical Infarction", *Circulation*, 99, (1999), pp. 135-142.

Kelly, E. B., "Advances in Mammalian and Stem Cell Cloning", *Genetic Engineering News*, vol. 23, No. 7, (Apr. 1, 2003), pp. 17-18 & 68.

Khademhosseini, et al., "Microscale Technologies for Tissue Engineering and Biology", *PNAS*, vol. 103, No. 8, (Feb. 21, 2006), pp. 2480-2487.

Kim, D., et al., "Glow Discharge Plasma Deposition (GDPD) Technique for the Local Controlled Delivery of Hirudin from Biomaterials", *Pharmaceutical Research*, 15(5), (1998), pp. 783-786.

Kim, Ung-Jin, et al., "Structure and Properties of Silk Hydrogels", *Biomacromolecules*, vol. 5(3), (2004), 786-792.

Kinart, et al., "Electrochemical Studies of 2-hydroxy-3-(3,4-dimethyl-9-oxo-9H-thioxanthen-2-yloxy)N,N,N-trimethyl-1-propanium chloride", *J. Electroanal. Chem*, 294, (1990), pp. 293-297.

Kipshidze, Nicholas, et al., "Therapeutic angiogenesis for critical limb ischemia to limit or avoid amputation", *University of Wisconsin Medical School, The Journal of Invasive Cardiology*, vol. 11, No. 1, (Jan. 1999), 25-28.

Klein, S., et al., "Fibroblast Growth Factors as Angiogenesis Factors: New Insights Into Their Mechanism of Action", *Regulation of Angiogenesis*, I.D. Goldberg and E.M. Rosen (eds.), 79, (1997), pp. 159-192.

Klugherz, Bruce D., et al., "Gene delivery from a DNA controlled-release stent in procine coronary arteries", *Nature Biotechnology*, vol. 18, (Nov. 2000), 1181-1184.

Kohilas, K, et al., "Effect of prosthetic titanium wear debris on mitogen-induced monocyte and lymphoid activation", *John Hopkins University, Dept. of Orthopaedic Surgery*, (Apr. 1999), 95-103.

Kweon, H. Y., et al., "Preparation of semi-interpenetrating polymer networks composed of silk fibroin and poly(ethyleneglycol) macromer", *Journal of Applied Polymer Science*, John Wiley and Sons Inc., New York, NY, vol. 80, (Jan. 2001), 1848-1853.

Kwok, C., et al., "Design of Infection-Resistant Antibiotic-Releasing Polymers: I. Fabrication and Formulation", *Journal of Controlled Release*, 62, (1999), pp. 289-299.

Laboratory of Liposome Research, "Liposomes: General Properties", downloaded from the Internet on Feb. 9, 2006 at www.unizh.ch/onkwww/lipos.htm.

Laham, R. J., "Intrapericardial Delivery of Fibroblast Growth Factor-2 Induces Neovascularization in a Porcine Model of Chronic Myocardial Ischemia", *J. Pharmacol Exper Therap*, 292(2), (2000), pp. 795-802.

Leibovich, S. J., et al., "Macrophage-Induced Angiogenesis is Mediated by Tumour Necrosis Factor-α", *Nature*, vol. 329, (Oct. 15, 1987), pp. 630-632.

Leor, J., et al., "Bioengineered Cardiac Grafts—A New Approach to Repair the Infarcted Myocardium?", *Circulation*, 102[suppl III], (2000), pp. III-56-III-61.

(56) References Cited

OTHER PUBLICATIONS

Leor, J., et al., "Gene Transfer and Cell Transplant: An Experimental Approach to Repair a 'Broken Heart'", *Cardiovascular Research*, 35, (1997), pp. 431-441.

Leroux, J. C., et al., "An Investigation on the Role of Plasma and Serum Opsonins on the Internalization of Biodegradable poly(D,L-lactic acid) Nanoparticles by Human Monocytes", *Life Sci.*, 57(7), Abstract downloaded from the Internet at www.ncbi.nlm.nih.gov/entrez/query.fcgi?cmd=Retrieve&db=pubmed, (1995), pp. 695-703.

Lewin, B., "Repressor is Controlled by a Small Molecule Inducer", *Genes VII*, Oxford University Press, 7th ed., (2000), pp. 277-280.

Li, et al., "Cell Therapy to Repair Broken Hearts", *Can. J. Cardiol.*, vol. 14, No. 5, (May 1998), pp. 735-744.

Li, W. W., et al., "Lessons to be Learned from Clinical Trials of Angiogenesis Modulators in Ischemic Diseases", *Angiogenesis in Health & Disease: Basic Mechanisms and Clinical Applications*, Rubanyi, G. (ed), Marcel Dekker, Inc. New York, (2000), Chapter 33.

Li, J., et al., "PR39, A Peptide Regulator of Angiogenesis", *Nature Medicine*, 6(1), (Jan. 2000), pp. 49-55.

Li, B., et al., "VEGF and PIGF promote adult vasculogenesis by enhancing EPC recruitment and vessel formation at the site of tumor neovascularization", *The FASEB Journal*, vol. 20, (2006), 1495-1497.

Li., Y. Y., et al., "Differential Expression of Tissue Inhibitors of Metalloproteinases in the Failing Human Heart", *Circulation*, 98(17), (1998), pp. 1728-1734.

Lindsey, M., et al., "Selective Matrix Metalloproteinase Inhibition Reduces Left Ventricular Remodeling but does not Inhibit Angiogenesis after Myocardial Infarction", *Circulation*, 105(6), (2002), pp. 753-758.

Long, D. M., et al., "Self-Cleaving Catalytic RNA", *FASEB Journal*, 7, (1993), pp. 25-30.

Lopez, J. J., et al., "Angiogenic potential of perivascular delivered aFGF in a porcine model of chronic myocardial ischemia", *The American Physiological Society*, 0363-6135/98, (1998), H930-H936.

Lopez, J. J., et al., "VEGF Administration in Chronic Myocardial Ischemia in Pigs", *Cardiovasc. Res.*, 40(2), Abstract downloaded from the Internet at: http://www.ncbi.nlm.nih.gov/entrez/query.fcgi?cmd=Retrieve&db=pubmed, 1 page, (1998), pp. 272-281.

Lu, L., et al., "Biodegradable Polymer Scaffolds for Cartilage Tissue Engineering", *Clinical Orthopaedics and Related Research*, Carl T. Brighton (ed.). No. 391S, (2001), pp. S251-S270.

Luo, Y., et al., "Cross-linked Hyaluronic Acid Hydrogel Films: New Biomaterials for Drug Delivery", *Journal of Controlled Release*, 69, (2000), pp. 169-184.

Lutolf, M, et al., "Synthesis and Physicochemical Characterization of End-Linked Poly(ethylene glycol)-co-peptide Hydrogels Formed by Michael-Type Addition", *Biomacromolecules*, vol. 4, (2003), 713-722.

Lyman, M. D., et al., "Characterization of the Formation of Interfacially Photopolymerized Thin Hydrogels in Contact with Arterial Tissue", *Biomaterials*, 17(3), (1996), pp. 356-364.

Mansour, S., et al., "Disruption of the proto-oncogene int-2 in mouse embryo-derived stem cells: a general strategy for targeting mutations to non-selectable genes", *Nature*, 336, (1988), pp. 348-352.

Martin, S. L., et al., "Total Synthesis and Expression in *Escherichia coli* of a Gene Encoding Human Tropoelastin", *Gene*, (1995), Abstract.

McDevitt, T., et al., "In vitro Generation of Differentiated Cardiac Myofibers on Micropatterned Laminin Surfaces", *J. Biomed Mater Res.*, 60, (2002), 472-479.

Meinel, L., et al., "The Inflammatory Responses to Silk Films In Vitro and In Vivo", *Biomaterials*, vol. 26, (2005), 147-155.

Mogan, L., "Rationale of platelet gel to augment adaptive remodeling of the injured heart", *J Extra Corpor Technol*, 36(2), (Jun. 2004), 191-196.

Narmoneva, D. A., et al., "Self-assembling short oligopeptides and the promotion of angiogenesis", *Biomaterials*, 26, (2005), pp. 4837-4846.

Nazarov, R., et al., "Porous 3-D Scaffolds from Regenerated Silk Fibroin", *Biomacromolecules*, vol. 5(3), (2004), 718-726.

Nguyen, K. T., et al., "Photopolymerizable Hydrogels for Tissue Engineering Applications", *Biomaterials*, 23, (2002), pp. 4307-4314.

Nikolic, S. D., et al., "New Angiogenic Implant Therapy Improves Function of the Ischemic Left Venticle", *Supplement to Circulation; Abstracts From Scientific Sessions 2000*, 102(18), (Oct. 2000), pp. II-689, Abstract 3331.

Nikolic, Serjan D., et al., "Novel means to improve coronary blood flow", *Clinical Science, Abstracts from Scientific Sessions*, (2000), II-689.

Nitinol Technical Information, "NiTi Smart Sheets", downloaded from the Internet on Dec. 10, 2002 at: http://www.sma-inc.com/information.html, 1 page.

Nose, et al., "A novel cadherin cell adhesion molecule: its expression patterns associated with implantation and organogenesis of mouse embryos", *Journal of Cell Biology*, vol. 103 (No. 6, Pt. 2), The Rockefeller University Press, (Dec. 1986), 2649-2658.

Ohyanagi, H., et al., "Kinetic Studies of Oxygen and Carbon Dioxide Transport into or from Perfluorochemical Particles", *Proc. ISAO*, vol. 1 (Artificial Organs vol. 2 (Suppl.)), (1977), pp. 90-92.

Ozbas, B., et al., "Salt-Triggered Peptide Folding and Consequent Self-Assembly into Hydrogels with Tunable Modulus", *Macromolecules*, 37(19), (2004), pp. 7331-7337.

Ozbas-Turan, S., "Controlled Release of Interleukin-2 from Chitosan Microspheres", *Journal of Pharmaceutical Sciences*, 91(5), (May 2002), pp. 1245-1251.

Palmiter, R., et al., "Germ-Line Transformation of Mice", *Ann. Rev. Genet.*, 20, (1986), pp. 465-499.

Patrick, C. R., "Mixing and Solution Properties of Organofluorine Compounds", *Preparation, Properties and Industrial Applications of Organofluorine Compounds*, Chapter 10, R.E. Banks (ed.), 1st edition, Ellis-Horwood Ltd., Chichester:England, (1982), pp. 323-342.

Peattie, R. A., et al., "Stimulation of In Vivo Angiogenesis by Cytokine-Loaded Hyaluronic Acid Hydrogel Implants", *Biomaterials*, 25(14), Abstract downloaded from: www.sciencedirect.com, (Jun. 2004).

Penta, K., et al., "Del1 Induces Integrin Signaling and Angiogenesis by Ligation of $\alpha V\beta 3$", *J. Biolog. Chem.*, 274(16), (Apr. 1999), pp. 11101-11109.

Perin, E. C., et al., "Transendocardial, Autologous Bone Marrow Cell Transplantation for Severe, Chronic, Ischemic Heart Failure", *Circulation*, (2003).

Pouzet, B., et al., "Is Skeletal Myoblast Transplantation Clinically Relevant in the Era of Angiotensin-Converting Enzyme Inhibitors?", *Circulation*, 104 [suppl I], (Sep. 2001), pp. I-223-I-228.

Prather, et al., "Nuclear Transplantation in Early Pig Embryos", *Biol. Reprod.*, 41, (1989), pp. 414-418.

Prosci Incorporated, "ILPIP (CT) Peptide".

Quellec, P., et al., "Protein Encapsulation Within Polyethylene Glycol-coated Nanospheres. I. Physicochemical Characterization", *J. Biomed. Mater. Res.*, 42(1), (1998)), Abstract.

Ramirez-Solis, R., et al., "Gene Targeting in Embryonic Stem Cells", *Methods in Enzymology*, 225, (1993), pp. 855-878.

Ritter, A. B., et al., "Elastic modulus, distensibility, and compliance (capacitance)", *Biomedical Engineering Principles*, Chapter 4, (2005), 187-191.

Rowley, et al., "Alginate Hydrogels as Synthetic Extracelllular Matrix Materials", *Biomaterials*, 20(1), (1999), 45-53.

Sawhney, A. S., et al., "Bioerodible Hydrogels Based on Photopolymerized Poly(ethylene glycol)-co-poly(a-hydroxy acid) Diacrylate Macromers", *Macromolecules*, 26(4), (1993), pp. 581-587.

Sbaa-Ketata, E., et al., "Hyaluronan-Derived Oligosaccharides Enhance SDF-1-Dependent Chemotactic Effect on Peripheral Blood Hematopoietic CD34+ Cells", *Stem Cells*, 20(6), Letter to the Editor downloaded from the Internet at www.stemcells.alphamedpress.org/cgi/content/full/20/6/585, (2002), 585-587.

(56) References Cited

OTHER PUBLICATIONS

Seeger, J. M., et al., "Improved in vivo endothelialization of prosthetic grafts by surface modification with fibronectin", *J Vasc Surg*, vol. 8, No. 4, (Oct. 1988), 476-82 (Abstract ony).
Segura, T , et al., "Crosslinked Hyaluronic Acid Hydrogels: A Strategy to Functionalize and Pattern", *Biomaterials*, vol. 26(4), (Feb. 2005), 359-371.
Segura, T , et al., "DNA delivery from hyaluronic acid-collagen hydrogels via a substrate-mediated approach", *Biomaterials*, vol. 26, (2005), 1575-1584.
Segura, T. , et al., "Substrate-Mediated DNA Delivery: Role of the Cationic Polymer Structure and Extent of Modification", *Journal of Controlled Release*, 93, (2003), pp. 69-84.
Segura, T. , et al., "Surface-Tethered DNA Complexes for Enhanced Gene Delivery", *Bioconjugate Chem*, 13(3), (2002), pp. 621-629.
Shibasaki, F. , et al., "Suppression of Signalling Through Transcription Factor NF-AT by Interactions Between Calcineurin and Bcl-2", *Nature*, 386(6626), Abstract downloaded from the Internet at www.ncbi.nlm.nih.gov/entrez/query.fcgi?CMD=Text&DB=pubmed, (1997).
Shin, H. , et al., "Attachment, Proliferation, and Migration of Marrow Stromal Osteoblasts Cultured on Biomimetic Hydrogels Modified with an Osteopontin-Derived Peptide", *Biomaterials*, 25, (2004), pp. 895-906.
Shin, H. , et al., "In vivo bone and soft tissue response to injectable, biodegradable oligo(poly(ethylene glycol) fumarate) hydrogels", *Biomaterials 24*, Elseview Science Ltd., (3201-3211), 2003.
Shu, Z , et al., "Disulfide-crosslinked hyaluronan-gelatin hydrogel films: a covalent mimic of the extracellular matrix for in vitro cell growth", *Biomaterials*, vol. 24(21), (Sep. 2003), 3825-3834.
Shu, Zheng , et al., "In situ crosslinkable hyaluronan hydrogels for tissue engineering", *Biomaterials*, vol. 25, No. 7-8, (Mar. 2004), 1339-1348.
Simons, M. , et al., "Clinical trials in coronary angiogenesis: Issues, problems, consensus, An expert panel summary", *Angiogenesis Research Center, American Heart Association, Inc.,*, (Sep. 12, 2000), 1-14.
Spenlehauer, G , et al., "In vitro and in vivo degradation of poly(D,L lactide/glycolide) type microspheres made by solvent evaporation method", *Biomaterials*, vol. 10, (Oct. 1989), 557-563.
Spinale, F. G., "Matrix Metalloproteinases—Regulation and Dysregulation in the Failing Heart", *Circ. Res.*, 90, (2002), pp. 520-530.
Springer, M. , et al., "Angiogenesis Monitored by Perfusion with a Space-Filling Microbead Suspension", *Mol. Ther.*, 1(1), Abstract downloaded from the Internet at www.ncbi.nlm.nih.gov/entrez/query.fcgi?cmd=Retrieve&db=PubMed, (2000), pp. 82-87.
Staatz, WD , et al., "Identification of a tetrapeptide recognition sequence for the alpha 2 beta 1 integrin in collagen", *Journal of Biological Chemistry*, 1991, 266(12), pp. 7363-7367.
Storm, G. et al., "Surface Modification of Nanoparticles to Oppose Uptake by the Mononuclear Phagocyte System", *Advanced Drug Delivery Reviews*, 17(1), Abstract downloaded from the Internet at www.sciencedirect.com, (Oct. 1995), pp. 31-48.
Strauer, B. , et al., "Repair of Infarcted Myocardium by Autologous Intracoronary Mononuclear Bone Marrow Cell Transplantation in Humans", *Cirulation*, 106, (2002), pp. 1913-1918.
Tybulewicz, V. , et al., "Neonatal lethality and lymphopenia in mice with a homozygous disruption of the c-abl proto-oncogene", *Cell*, 65(7), Abstract downloaded from the Internet at www.sciencedirect.com, (Jun. 1991), pp. 1153-1163.
Unger, E. F., et al., "Effects of a Single Intracoronary Injection of Basic Fibroblast Growth Factor in Stable angina Pectoris", *Am. J. Cardiol*, 85(12), Abstract downloaded from the Internet at www.sciencedirect.com, (Jun. 2000), pp. 1414-1419.

Urbich, C. , et al., "Endothelial Progenitors Cells: Characterization and Role in Vascular Biology", *Circulation Research*, vol. 95, (2004), 343-353.
Van Der Giessen, Willem J., et al., "Marked inflammatory sequelae to implantation of biodegradable and nonbiodegradable polymers in porcine coronary arteries", *Dept. of Cardiology, Erasmus University Rotterdam, Circulation*, vol. 94, No. 7, (Oct. 1, 1996), 1690-1697.
Van Luyn, M. J., et al., "Cardiac Tissue Engineering: Characteristics of in Unison Contracting Two- and Three-Dimensional Neonatal Rat Ventricle Cell (Co)-Cultures", *Biomaterials*, 23, (2002), pp. 4793-4801.
Vercruysse, K. P., et al., "Synthesis and in Vitro Degradation of New Polyvalent Hydrazide Cross-Linked Hydrogels of Hyaluronic Acid", *Bioconjugate Chem*, 8(5), Abstract downloaded from the Internet at pubs.acs.org/cgi-bin/abstract.cgi/bcches/1997/8/i05/abs/bc9701095.html, (1997), pp. 686-694.
Visscher, G.E. et al., "Tissue response to biodegradable injectable microcapsules", *Journal of Biomaterials Applications*, vol. 2, (Jul. 1987), 118-119.
Vlodavsky, I. et al., "Extracellular Matrix-resident Basic Fibroblast Growth Factor: Implication for the Control of Angiogenesis", *J. Cell Biochem*, 45(2), Abstract downloaded from the Internet at www.ncbi.nlm.nih.gov/entrez/query.fcgi?cmd=Retrieve&db=PubMed, (Feb. 1991), pp. 167-176.
Wang M. , et al., "Mechanical Properties of Electrospun Silk Fibers", *Macromolecules*, vol. 37(18), (2004), 6856-6864.
Wasielewski, "Ischamische Erkrankungen, Gefassneubildung anregen", *Deutsche Apotheker Zeitung*, vol. 140, No. 3, Stuttgart (DE), (Jan. 20, 2000), 232-233.
Wilensky, R. , et al., "Direct intraarterial wall injection of microparticles via a catheter: a potential drug delivery strategy following angioplasty", *American Heart Journal*, 122, (1991), p. 1136.
Witzenbichler, B. , et al., "Vascular Endothelial Growth Factor-C (VEGF-C/VEGF-2) Promotes Angiogenesis in the Setting of Tissue Ischemia", *AM Pathol.*, 153(2), (Aug. 1998), pp. 381-394.
Yager, P. , et al., "Silk Protein Project", www.faculty.washington.edu/yagerp/silkprojecthome.html, (Aug. 23, 1997), pp. 1-16.
Yamamoto, N. , et al., "Histologic evidence that basic fibroblast growth factor enhances the angiogenic effects of transmyocardial laser recascularization", *Basic Research in Cardiology*, vol. 95, No. 1, (Feb. 1, 2000), 55-63.
Yeo, L.Y. , et al., "AC Electrospray Biomaterials Synthesis", *Biomaterials*, (2005), 7 pages.
Zervas, L. , et al., "On Cysteine and Cystine Peptides. II. S-Acylcysteines in Peptide Synthesis", *J. Am. Chem. Soc.*, 85(9), (May 1963), pp. 1337-1341.
Zheng, Shu , et al., "In situ crosslinkable hyaluronan hydrogels for tissue engineering", *Biomaterials, Elsevier Science Publishers*, vol. 25, No. 7-8, (2004), 1339-1348.
Zheng, W. , "Mechanisms of coronary angiogenesis in response to stretch; role of VEGF and TGF-Beta", *Am J Physiol Heart Circ Physiol 280*(2), (Feb. 2001), H909-H917.
Zimmermann, W. , et al., "Engineered Heart Tissue for Regeneration of Diseased Hearts", *Biomaterials*, 25, (2004), pp. 1639-1647.
Abbot Cardiovascular Systems, Office Action dated May 23, 2016 for U.S. Appl. No. 14/685,474,11 pages.
Abbott Cardiovascular Systems, Office Action dated Apr. 19, 2016 for U.S. Appl. No. 13/898,413,12 pages.
Abbott Cardiovascular Systems, Restriction Requirement dated Feb. 8, 2016 for U.S. Appl. No. 13/898,413, 10 pages.
Robinson et al. "Extracellular Matrix Scaffold for Cardiac Repair", Circulation, http://wwwcirculationaha.org, 2005, vol. 104, pp. I-135-I1-143.
Abbott Cardiovascular Systems, Notice of Allowance dated Oct. 20, 2016, for U.S. Appl. No. 13/898,413, 9 pages.

* cited by examiner

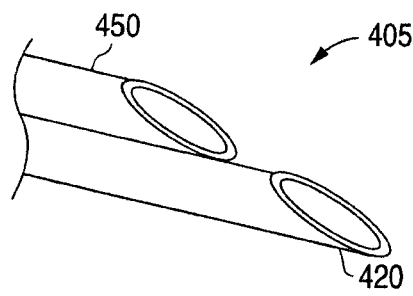
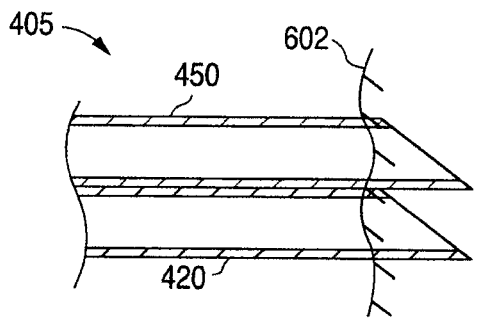
FIG. 11A          FIG. 11C
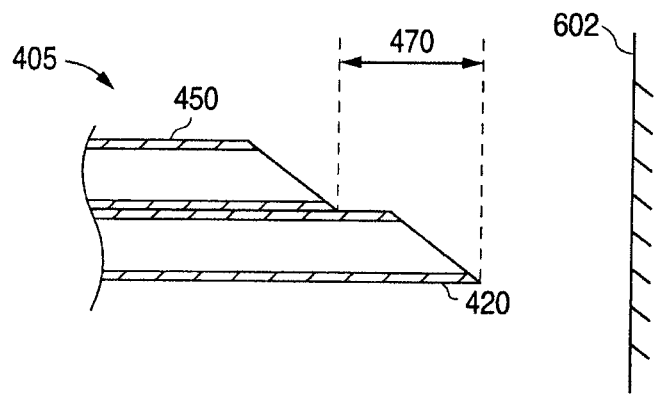
FIG. 11B
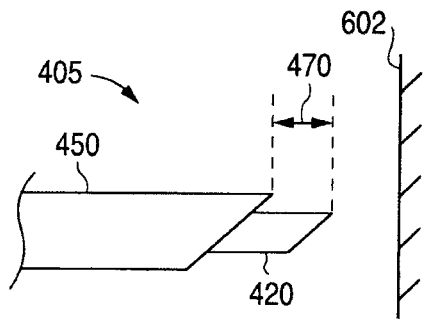
FIG. 12A

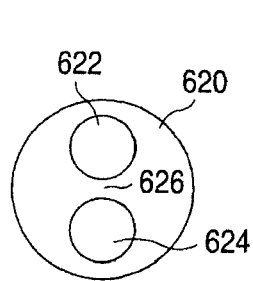 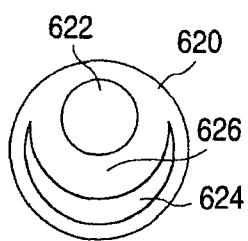 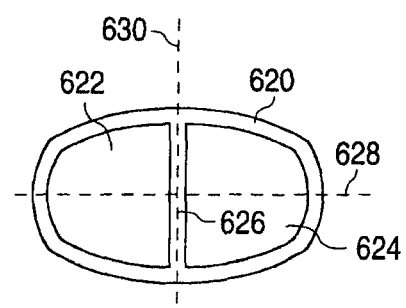
FIG. 14A    FIG. 14B    FIG. 14C
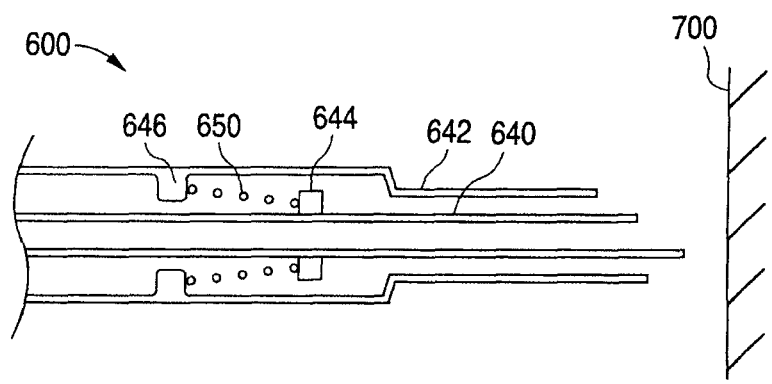
FIG. 15A
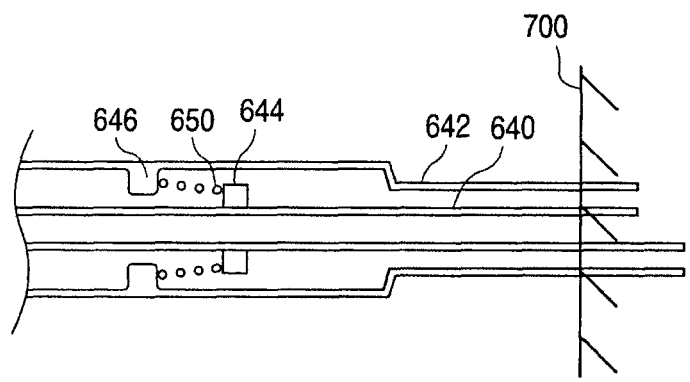
FIG. 15B

METHODS AND COMPOSITIONS FOR TREATING POST-CARDIAL INFARCTION DAMAGE

CROSS REFERENCE TO RELATED APPLICATIONS

This is a continuation of U.S. application Ser. No. 12/963,397, filed Dec. 8, 2010, now abandoned, which is a divisional of U.S. application Ser. No. 11/978,986, filed Oct. 29, 2007, now abandoned which is a continuation-in-part of U.S. application Ser. No. 11/447,340, filed Jun. 5, 2006, now U.S. Pat. No. 8,187,621, which is a continuation-in-part of U.S. application Ser. No. 11/361,920, filed Feb. 23, 2006, now U.S. Pat. No. 8,303,972, which is a continuation-in-part of U.S. application Ser. No. 11/110,223, filed Apr. 19, 2005, now U.S. Pat. No. 8,828,433, all of which are incorporated by reference herein.

FIELD OF THE INVENTION

Post-myocardial infarction treatments and compositions.

BACKGROUND OF THE INVENTION

Ischemic heart disease typically results from an imbalance between the myocardial blood flow and the metabolic demand of the myocardium. Progressive atherosclerosis with increasing occlusion of coronary arteries leads to a reduction in coronary blood flow. "Atherosclerosis" is a type of arteriosclerosis in which cells including smooth muscle cells and macrophages, fatty substances, cholesterol, cellular waste product, calcium and fibrin build up in the inner lining of a body vessel. "Arteriosclerosis" refers to the thickening and hardening of arteries. Blood flow can be further decreased by additional events such as changes in circulation that lead to hypoperfusion, vasospasm or thrombosis.

Myocardial infarction (MI) is one form of heart disease that often results from the sudden lack of supply of oxygen and other nutrients. The lack of blood supply is a result of a closure of the coronary artery (or any other artery feeding the heart) which nourishes a particular part of the heart muscle. The cause of this event is generally attributed to arteriosclerosis in coronary vessels.

Formerly, it was believed that an MI was caused from a slow progression of closure from, for example, 95% then to 100%. However, an MI can also be a result of minor blockages where, for example, there is a rupture of the cholesterol plaque resulting in blood clotting within the artery. Thus, the flow of blood is blocked and downstream cellular damage occurs. This damage can cause irregular rhythms that can be fatal, even though the remaining muscle is strong enough to pump a sufficient amount of blood. As a result of this insult to the heart tissue, scar tissue tends to naturally form.

Various procedures, including mechanical and therapeutic agent application procedures, are known for reopening blocked arties. An example of a mechanical procedure includes balloon angioplasty with stenting, while an example of a therapeutic agent application includes the administration of a thrombolytic agent, such as urokinase. Such procedures do not, however, treat actual tissue damage to the heart. Other systemic drugs, such as ACE-inhibitors and Beta-blockers, may be effective in reducing cardiac load post-MI, although a significant portion of the population that experiences a major MI ultimately develop heart failure.

An important component in the progression to heart failure is remodeling of the heart due to mismatched mechanical forces between the infracted region and the healthy tissue resulting in uneven stress and strain distribution in the left ventricle. Once an MI occurs, remodeling of the heart begins. The principle components of the remodeling event include myocyte death, edema and inflammation, followed by fibroblast infiltration and collagen deposition, and finally scar formation. The principle component of the scar is collagen. Since mature myocytes of an adult are not regenerated, the infarct region experiences significant thinning Myocyte loss is the major etiologic factor of wall thinning and chamber dilation that may ultimately lead to progression of cardiac myopathy. In other areas, remote regions experience hypertrophy (thickening) resulting in an overall enlargement of the left ventricle. This is the end result of the remodeling cascade. These changes in the heart result in changes in the patient's lifestyle and their ability to walk and to exercise. These changes also correlate with physiological changes that result in increase in blood pressure and worsening systolic and diastolic performance.

SUMMARY OF THE INVENTION

A device comprising: a first delivery needle, and a second delivery needle, a biasing element associated with the first delivery needle and the second delivery needle, wherein the first delivery needle and the second delivery needle are arranged in a side-by-side configuration, whereby a first gel component can be delivered through the first delivery needle without contacting a second gel component that may be disposed in the second delivery needle.

BRIEF DESCRIPTION OF THE DRAWINGS

FIGS. 11A-11C illustrate an alternative embodiment of a needle assembly having offset needles that can be used to deliver the compositions of the present invention;

FIGS. 12A-12C illustrate an alternative embodiment of a needle assembly having offset needles that can be used to deliver the compositions of the present invention;

FIGS. 14A-14C illustrate alternative embodiments of a delivery needle in accordance with the present invention;

FIGS. 15A-15B illustrate an alternative embodiment of a needle assembly having biased offset needles that can be used to deliver the compositions of the present invention;

DETAILED DESCRIPTION

Methods and compositions for treating post-myocardial infarction damage are herein disclosed. In some embodiments, a carrier with a treatment agent may be fabricated. The carrier can be formulated from a bioerodable, sustained-release substance. The resultant loaded carrier may then be suspended in at least one component of a two-component matrix system for simultaneous delivery to a post-myocardial infarction treatment area.

Figure 1A:
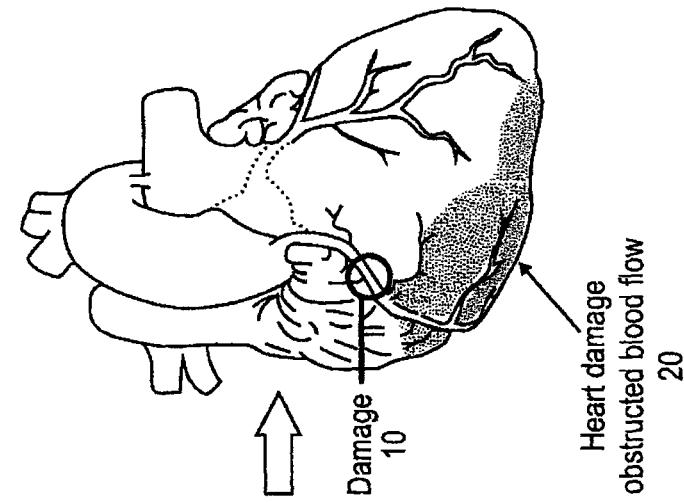
FIGS. 1A-1B illustrate the progression of heart damage once the build-up of plaque in an artery induces an infarct to occur.
Figure 1B:
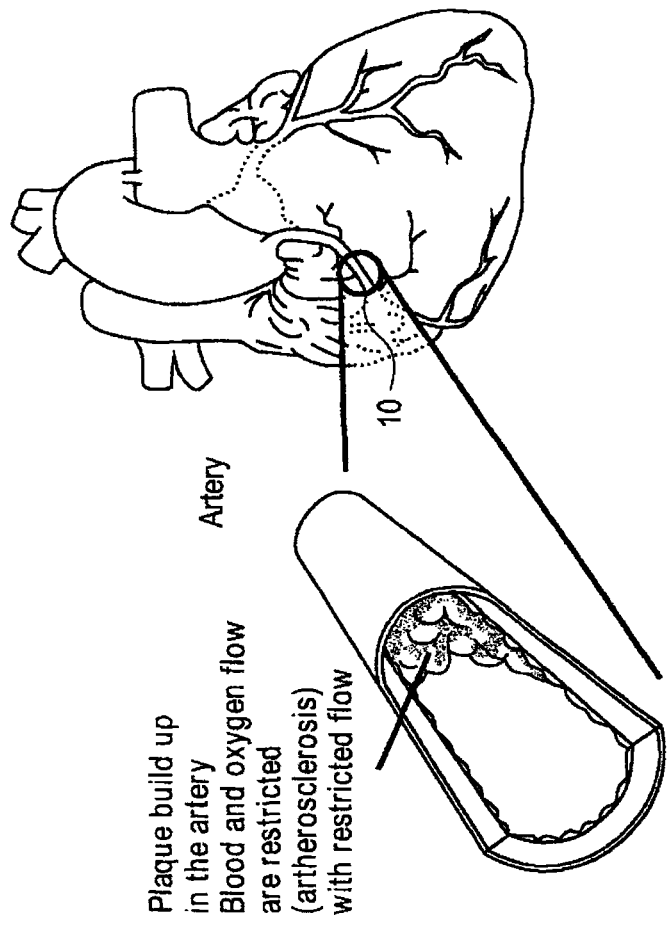

FIGS. 1A-1B illustrate the progression of heart damage once the build-up of plaque induces an infarct to occur. FIG. 1A illustrates a site 10 where blockage and restricted blood flow can occur from, for example, a thrombus or embolus. FIG. 1B illustrates resultant damage area 20 to the left ventricle that can result from the lack of oxygen and nutrient flow carried by the blood to the inferior region left of the heart. The damage area 20 will likely undergo remodeling, and eventually scarring, resulting in a non-functional area.

Treatment Agents

Treatment agents to treat post-myocardial infarction treatment areas may include: (i) agents that promote angiogenesis (angiogenesis promoting factors); (ii) agents that promote cell survival (cell survival promoting factors); and (iii) agents that recruit endogenous progenitor and/or stem cells (endogenous recruiting factors). Various forms of treatment agents are intended to include, but are not intended to be limited to, drugs, biologically active agents, chemically active agents, therapeutic agents, and the like, and pharmaceutical compositions thereof, which can be used in the delivery of a treatment agent to a treatment site as described herein.

"Angiogenesis" is the promotion or causation of the formation of new blood vessels. After an MI, the infarct tissue as well as the border zone and the remote zone around the infarct tissue begin to remodel. Scar tissue forms in the infarct region as the granulation is replaced with collagen. Stress from blood pressure cause the scar to thin out and stretch. The perfusion in this region is typically 10% of the healthy zone, decreasing the number of active capillaries. Increasing the number of capillaries may lead to an increase in compliance of the ventricle due to filling up with blood. Other benefits of increasing blood flow to the infarcted region include providing a route for circulating stem cells to seed and proliferate in the infarct region. Angiogenesis may also lead to increased oxygenation for the surviving cellular islets within the infarct region, or to prime the infarct region for subsequent cell transplantation for myocardial regeneration. In the border zone, surviving cells would also benefit from an increase in blood supply through an angiogenesis process. In the remote zone, where cardiac cells tend to hypertrophy and become surrounded with some interstitial fibrosis, the ability of cells to receive oxygen and therefore function to full capacity are also compromised; thus, angiogenesis would be beneficial in these regions as well.

In some embodiments, angiogenesis promoting factors include, but are not intended to be limited to, growth factors such as isoforms of vasoendothelial growth factor (VEGF), fibroblast growth factor (FGF, e.g. beta-FGF), Del 1, hypoxia inducing factor (HIF 1-alpha), monocyte chemoattractant protein (MCP-1), nicotine, platelet derived growth factor (PDGF), insulin-like growth factor 1 (IGF-1), transforming growth factor (TGF alpha), hepatocyte growth factor (HGF), estrogens, follistatin, proliferin, prostaglandin E1 and E2, tumor necrosis factor (TNF-alpha), interleukin 8 (Il-8), hematopoietic growth factors, erythropoietin, granulocyte-colony stimulating factors (G-CSF) and platelet-derived endothelial growth factor (PD-ECGF). In some embodiments, angiogenesis promoting factors include, but are not intended to be limited to, peptides, such as PR39, PR11 and angiogenin, small molecules, such as PHD inhibitors, or other agents, such as eNOS enhancers.

Endogenous cardiomyocyte (myocytes) apoptosis is the major etiological factor of wall thinning and chamber dilation and may ultimately lead to progression of cardiac myopathy. After an infarction, mature myocytes of an adult are not regenerated which can lead to significant thinning in the infarct region. Thus, factors which promote cell survival applied to the infarct region are believed to be beneficial. In some embodiments, cell survival promoting factors include, but are not intended to be limited to, growth factors such as insulin-like growth factor (IGF-1) and human growth factor (HGF), which are known to mediate cell growth, differentiation and survival of a variety of cell types. In addition, small molecules such as, for example, HMG-CoA reductase inhibitors (statins) and capsase inhibitors can also promote cell survival and inhibit apoptosis.

To assist in the generation of new cells at the infarct region, autologous or allogeneic stem cells may be delivered to a patient. "Autologous" means the donor and recipient of the stem cells are the same. "Allogeneic" means the donor and recipient of the stem cells are different. Cell survival promoting factors can also be used to increase the survivability of autologous and allogeneic implanted stem cells at the infarct region.

Cardiac progenitor cells are highly specialized stem cells which have shown the ability to differentiate into certain types of fully mature cardiac tissue. Examples of cardiac progenitor cells include, but are not limited to, c-Kit(+), Sca-1(+) and Isl-1(+). Thus, factors which recruit endogenous factors when applied to the infarct region are believed to be beneficial. In some embodiments, an endogenous recruiting factor can include, for example, HGF. HGF has been shown to control cell motility and promote cell migration. If applied post-infarction, HGF can assist in mobilizing and recruiting resident cardiac progenitor cells to the infarct region. In some embodiments, an endogenous recruiting factor can include, but is not intended to be limited to, stromal cell-derived factor 1 (SDF-1). SDF-1 is the ligand for the CXCR4 receptor, which is a surface receptor on circulating endothelial progenitor cells. Thus, when applied in or around the infarct region, SDF-1 may facilitate the homing of circulating endothelial progenitor cells to induce neovascularization.

It is contemplated that any of the above-described treatment agents can be used singularly or in combination thereof. In addition, other treatment agents, including but not limited to, anti-inflammatory, anti-platelet, anti-coagulant, anti-fibrin, anti-thrombotic, anti-mitotic, anti-biotic, anti-allergic, anti-oxidant, anti-proliferative, or anti-migratory agents, may be optionally used singularly or in combination thereof.

Sustained-release Carriers

Bioerodable carriers (hereinafter interchangeably referred to as sustained-release carriers) infused with (or without) a treatment agent can be used for the sustained or controlled release of treatment agent for maximum benefit to the infarct region. It is believed that a large percentage of treatment agent delivered directly to the infarct region, or even diffused within a gel-like matrix, will be substantially washed away by the body's natural mechanisms, thus lessening the benefit of the treatment agent that may otherwise be obtained. Thus, sustained-release carriers infused with treatment agent that release the treatment agent over an extended time period can be beneficial by increasing the amount of time in which the infarct region is exposed to the treatment agent. Sustained-release carriers include, but are not limited to, (i) microparticles or nanoparticles (hereinafter interchangeably referred to as microparticles), (ii) microfibers or nanofibers (hereinafter interchangeably referred to as microfibers) and (iii) liposomes and polymerosomes.

In addition, in some embodiments, a bioerodable carrier may be infused with (or without) a treatment agent and delivered to a treatment site to act as a "docking site" for endogenous myocardial stem cells and encourage their differentiation into cardiomyocytes.

A.

In some embodiments, the sustained-release carrier is a microparticle. Various methods can be employed to formulate and infuse or load the microparticles with treatment agent. In some embodiments, the microparticles are prepared by a water/oil/water (W/O/W) double emulsion method. In the W1 phase, an aqueous phase containing treatment agent, is dispersed into the oil phase consisting of polymer dissolved in organic solvent (e.g., dichloromethane) using a high-speed homogenizer. Examples of sustained-release polymers include, but are not limited to, poly(D,L-lactide-co-glycolide) (PLGA), poly(D,L-lactide) (PLA) or PLA-PEEP co-polymers, poly-ester-amide co-polymers (PEA) and polyphophazines. The primary water-in-oil (W/O) emulsion is then dispersed to an aqueous solution containing a polymeric surfactant, e.g., poly(vinyl alcohol) (PVA), and further homogenized to produce a W/O/W emulsion. After stirring for several hours, the microparticles are collected by filtration.

B.

In some embodiments, the sustained-release carrier is a microfiber or nanofiber. For example, the treatment agent (or no treatment agent) infused microfiber can be formulated by electrospinning "Electrospinning" is a process by which microfibers are formed by using an electric field to draw a polymer solution from the tip of a capillary to a collector. A voltage is applied to the polymer solution which causes a stream of solution to be drawn toward a grounded collector. Electrospinning generates a web of fibers which can be subsequently processed into smaller lengths.

Examples of sustained-release polymers which can be used in electrospinning include, but are not limited to, PLGA, PLA or PLA-PEEP co-polymers, PEA, polyphosphazines and collagen. In one method, the treatment agent is mixed with a bioerodable polymer solution, a solvent and a surfactant. Examples of surfactants can include, but are not limited to, anionic or cationic surfactants. Useful anionic surfactants include, but are not intended to be limited to, bis(2-ethylhexyl)sodium sulfosuccinate (AOT), bis(2-ethylhexyl)phosphate (NaDEHP), tauroglycocholate, and sodium lauryl sulfate. A useful cationic surfactant is tetradecyltrimethyl-ammonium bromide (TTAB). An example of a solvent includes, but is not limited to, hexafluoro isopropanol. The treatment agent-infused polymer solution is then subjected to electrospinning. As the solvent evaporates during electrospinning, the treatment agent incorporates and distributes within the polymer by non-covalent interactions. The resultant microfibers which can be from about 0.5 μm to about 3 μm in diameter form a web which may then be processed into smaller lengths of about 0.5 μm to about 500 μm. Based on the treatment agent, in some applications, microfibers may be a preferred sustained-release carrier due to the non-aqueous process by which they are formed. In some applications, microspheres may be preferable when the treatment agent is hydrophilic. In some applications, a microfiber is a preferred sustained-release carrier due to its release pharmacokinetic profile when compared to the release pharmacokinetic profile of a microsphere. In some cases, microspheres as well as microfibers can be used as a carrier of one or more than one treatment agent as the two types of carriers will provide different pharmacokinetic release profiles which may be advantageous for therapy.

In one embodiment, fibers can be electrospun from collagen and elastin dissolved in 1,1,1,3,3,3-hexafluoro-2-propanol (HFP), forming a polymer solution. A treatment agent can be added to the polymer solution. A surfactant and a stabilizer can be used to evenly disperse the treatment agent in the solvent. The polymer solution can then be loaded into a syringe and placed in a syringe pump for metered dispensing at a predetermined rate. A positive output lead of a high voltage supply can be attached to a needle on the syringe. The needle can be directed to a stainless steel grounded target placed approximately 10 cm from the needle tip, which can be rotated at a predetermined speed to ensure an even coating. The distance of the needle from the target can be varied depending upon the diameter of the fibers needed. The resultant microfibers are from about 0.5 μm to about 3 μm in diameter and the resulting non-woven mat of fibers can then be processed into smaller lengths of about 0.5 μm to about 500 μm.

C.

In some embodiments, the sustained-release carrier is a liposome or a polymerosome. "Liposomes" are artificial vesicles that are approximately spherical in shape and can be produced from natural phospholipids and cholesterol. In one method, phospholipids are mixed with cholesterol in chloroform. Suitable phospholipids include, but are not limited to, dimyristoyl phosphatidyl choline or dipalmitoyl ethanolamine. In some embodiments, hydrophobic treatment agent can be added with an optional co-solvent, such as heptane or toluene. The liposomes may also be hydrophilically modified with an agent such as polyethylene glycol or dextran. After mixing, the solvent (and optional co-solvent) can be evaporated with heat or ambient temperature in a round bottom flask. Resultant lipids will be deposited on the glass surface. In some embodiments, hydrophilic treatment agent and water can be added to the flask and sonicated to form liposomes. The resultant suspension can be pressure filtered through ceramic pore size controlled filters to reduce liposome particle size. In the case of a polymero some, a similar manufacturing technique can be used as that of a liposome. Polymerosomes can be formed from di-block co-polymers of differing solubility. For example, one block can be hydrophobic, e.g., poly lactic acid, polycaprolactone, n-butyl acrylate, and the other block can be hydrophilic, e.g., poly(ethylene glycol), poly(acrylic acid).

Matrix Systems

A biocompatible matrix system can be used to suspend the treatment agent or the treatment agent-infused sustained-release carrier for delivery to the infarct region. In some embodiments, the matrix system can be a one-component or a two-component gel. In some embodiments, the matrix system is a two-component gel. Two-component gels can include, for example, fibrin glues (e.g., two components comprising fibrinogen and thrombin), self-assembled peptides or alginate constructs.

In some embodiments, the matrix system is a one-component gel. An example of a one-component gel includes an acrylate agent that is biocompatible. The one-component gel serves in one aspect to disperse the sustained-release carrier in order to form a more uniform scaffold over the entire infarct zone and may include border zone as well. For example, the one-component gel may be sodium hyaluronate. The gel disperses the sustained-release carrier acting as a suspending media.

A.

In some applications, the two-component gelation system includes a fibrin glue. Fibrin glue consists of two main components, fibrinogen and thrombin. Fibrinogen is a plasma glycoprotein of about 340 kiloDaltons (kDa) in its endogenous state. Fibrinogen is a symmetrical dimer comprised of six paired polypeptide chains, alpha, beta and gamma chains. On the alpha and beta chains, there is a small peptide sequence called a fibrinopeptide which prevent fibrinogen from spontaneously forming polymers with itself. In some embodiments, fibrinogen is modified with proteins. Thrombin is a coagulation protein. When combined in equal volumes, thrombin converts the fibrinogen to fibrin by enzymatic action at a rate determined by the concentration of thrombin. The result is a biocompatible gel which gelates when combined at the infarct region. Fibrin glue can undergo gelation at about 10 to about 60 seconds. Examples of other fibrin glue-like systems include, but are not limited to, Tisseel™ (Baxter), CoSeal™ (Baxter), Crosseal™ (Omrix Biopharmaceuticals, Ltd.), Hemaseel® (Haemacure Corp.) and CoStasis® (Angiotech Pharmaceuticals).

B.

In some embodiments, the two-component gel comprises self-assembled peptides. Self-assembled peptides generally include repeat sequences of alternating hydrophobic and hydrophilic amino acid chains. The hydrophilic amino acids are generally charge-bearing and can be anionic, cationic or both. Examples of cationic amino acids are lysine and arginine. Examples of anionic amino acids are aspartic acid and glutamic acid. Examples of hydrophobic amino acids are alanine, valine, leucine, isoleucine or phenylalanine. Self-assembled peptides can range from 8 to about 40 amino acids in length and can assemble into nanoscale fibers under conditions of physiological pH and osmolarity. In sufficient concentration and over time, the fibers can assemble into an interconnected structure that appears macroscopically as a gel. Self-assembled peptides typically undergo gelation between several minutes to several hours. Examples of self-assembled peptides include, but are not limited to: AcN-RARADADARARADADA-CNH$_2$ (RAD 16-II) wherein R is arginine, A is alanine, D is aspartic acid, and Ac indicates acetylation; VKVKVKVKV-PP-TKVKVKVKV-NH$_2$ (MAX-1) wherein V is valine, K is lysine and P is proline; and AcN-AEAEAKAKAEAEAKAK-CNH$_2$ wherein A is alanine, K is lysine and E is glutamic acid (EAK16-II).

Example

In one example, the self-assembled peptide is RAD 16-II. At low pH and osmolarity, RAD 16-II forms a solution. At physiological pH and osmolarity, RAD 16-II forms a gel although gel formation can be slow. In some embodiments, RAD 16-II is mixed with phosphate buffer saline (PBS) to form a first component solution. In some embodiments, the first component solution can be co-injected with a second component comprising sodium chloride, sucrose or other osmolarity modifying substance using, for example, a dual-injection delivery assembly. In some embodiments, the components can be co-injected with carriers such as angiogenesis promoting factors, cell survival promoting factors and/or endogenous recruiting factors. These factors bind non-specifically to the self-assembled peptides by electrostatic interactions, and this binding can control or retard the release of the factors.

C.

In some embodiments, the two-component gel is an alginate construct. For example, the alginate construct may be collagen or gelatin grafted alginate. In one example, a first component can be a solution of about 0.5 percent to about 1.0 percent alginate while a second component can be a solution of about 40 mM to about 180 mM calcium chloride. One example of a suitable amount of components is about 200 microliters of alginate solution and about 200 microliters of calcium chloride. In one embodiment, a desired amount of a treatment agent may be introduced with the alginate solution.

Methods of Manufacture

Figure 2:
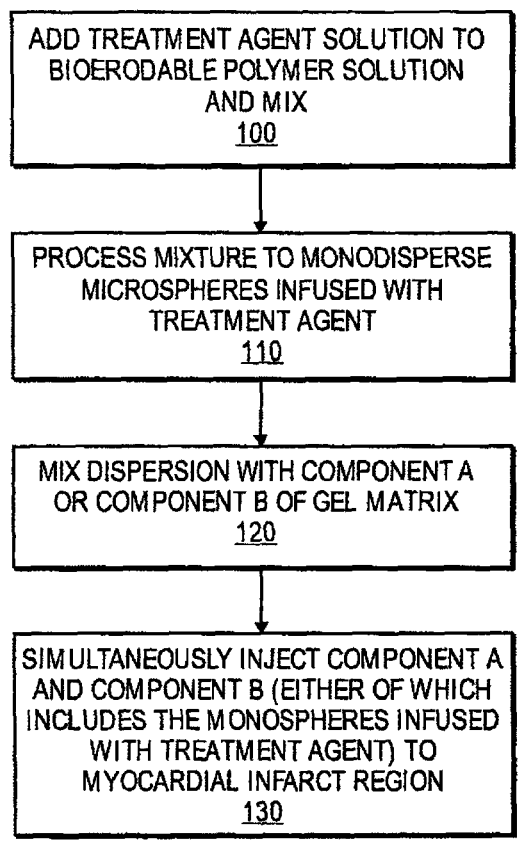
FIG. 2 schematically represents a method for preparing a two-component gel matrix with a sustained carrier loaded with treatment agent interdispersed therein.

FIG. 2 schematically represents a method for preparing a two-component gel matrix with a sustained carrier loaded with treatment agent interdispersed therein. A treatment agent, such as an angiogenesis promoting factor, cell survival promoting factor, endogenous recruiting factor or any combination thereof can be added to a bioerodable polymer such as PLGA or PEA and PLA-PEEP co-polymers or polyphosphazenes (100). In some embodiments, a W/O/W process can be used. The mixture can be processed to monodisperse the resultant treatment agent loaded microspheres (110). The microspheres can be in a range from about 5 µm to about 200 µm preferably from about 10 µm to about 50 µm. Next, the resultant dispersion can be added to one component of a two-component gel such as fibrin glue (120). In one embodiment, the two-component gel includes component A and component B, wherein component A is fibrinogen and component B is thrombin. Component A and component B can then be separately but simultaneously injected into the myocardial infarct region by a dual-injection delivery assembly for treatment thereof (130).

Figure 3:
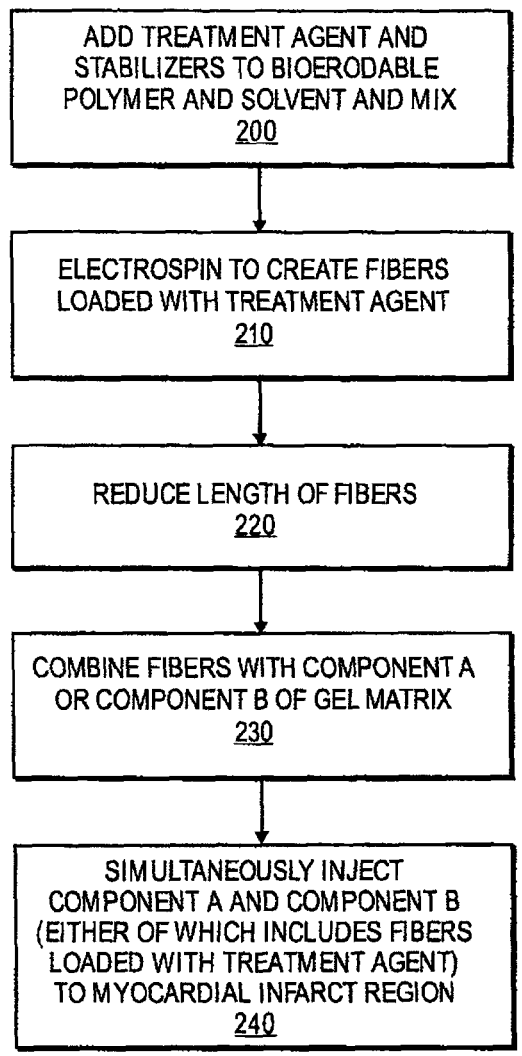
FIG. 3 schematically represents an alternative method for preparing a two-component gel matrix with a sustained carrier loaded with treatment agent interdispersed therein.

FIG. 3 schematically represents an alternative method for preparing a two-component gel matrix with a sustained carrier loaded with treatment agent interdispersed therein. A treatment agent, such as an angiogenesis promoting factor, cell survival promoting factor, endogenous recruiting factor or any combination thereof can be added to a bioerodable polymer such as PLGA or PEA and PLA-PEEP co-polymers or polyphosphazenes or collagen (200) with solvent. For collagen/elastin electrospun fibers, a suitable solvent can be HFP. In some embodiments, an aqueous system may be used. The mixture can then be subjected to electrospinning to create interwoven fibers (210) with a diameter in a range from about 0.2 μm to about 3 μm. The fibers may then be processed into smaller of length from about 0.5 μm to about 500 μm (220). The fibers may be processed by cryogenic grinding, subjected to ultrasound in water, or subjected to ultrasound in a volatile solvent that is a non-solvent for both the polymer and the encapsulated protein or other agent or subjected to any other suitable method to reduce their size. Next, the resultant fibers can be added to one component of a two-component gel such as fibrin glue (230). In one embodiment, the two-component gel includes component A and component B, wherein component A is fibrinogen and component B is thrombin. Component A and component B can then be separately but simultaneously injected into the myocardial infarct region by a dual-injection delivery assembly for treatment thereof (240).

Figure 4:
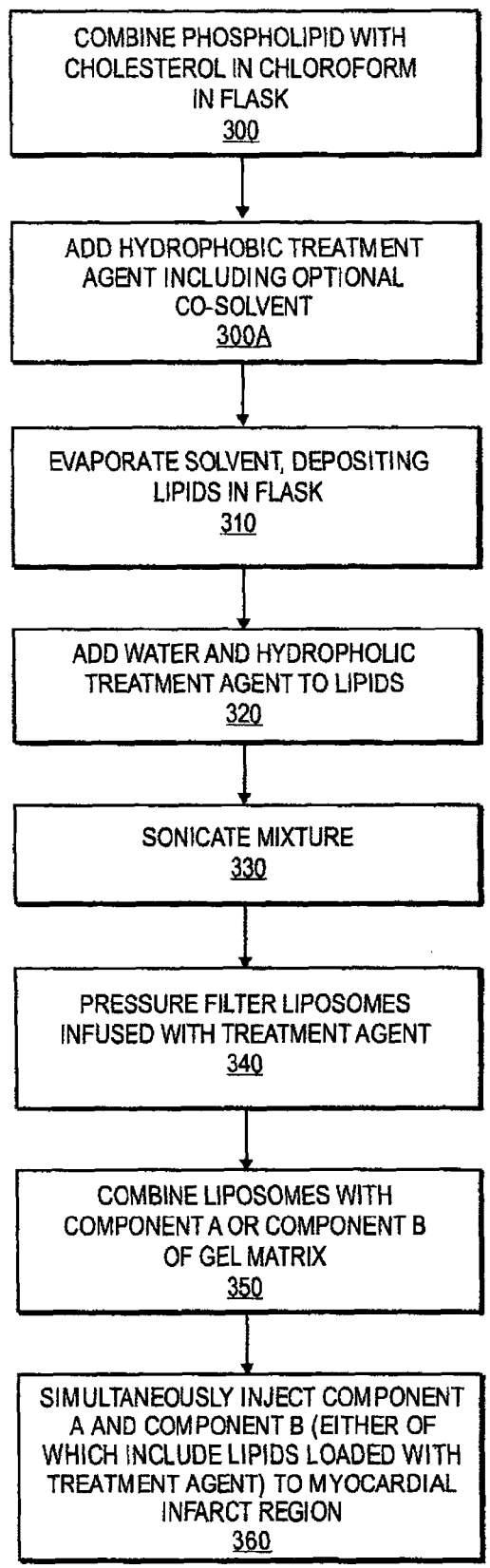
FIG. 4 schematically represents a second alternative method for preparing a two-component gel matrix with a sustained carrier loaded with treatment agent interdispersed therein.

FIG. 4 schematically represents another alternative method for preparing a two-component gel matrix with a sustained carrier loaded with treatment agent interdispersed therein. A phospholipid substance can be combined with cholesterol in a solvent such as chloroform (300) in a round bottom flask. In some embodiments, a hydrophobic treatment agent including an optional co-solvent can be added thereto (300A). The solvent(s) can be evaporated depositing lipids on the glass surface (310). Next, water is added and in some embodiments, a hydrophilic treatment agent (320). Then, the mixture is sonicated to form liposomes (330) and optionally pressure-filtered to reduce liposome particle size (340). Next, the resultant liposomes can be added to one component of a two-component gel such as fibrin glue (350). In one embodiment, the two-component gel includes component A and component B, wherein component A is fibrinogen and component B is thrombin. Component A and component B can then be separately but simultaneously injected into the myocardial infarct region by a dual-injection delivery assembly for treatment thereof (360).

Example

In one embodiment, collagen electrospun fibers can be processed to a range from about 200 nm and about 1300 nm. The range of electrospun fibers is approximately the range of naturally occurring type 1 and type 3 fibers which make up the heart matrix. Thus, the electrospun fibers may mimic endogenous fibers and accelerate growth of repair tissue to the infarct region, in particular, on the heart. The fibers can be dispersed throughout one component of a two-component gel. The two components can then be delivered to myocardial infarct region. The fibers can provide "docking sites" for endogenous myocardial stem cells and encourage their differentiation into cardiomyocytes. The gel can provide temporary containment of the fibers and prevent premature removal by macrophage cells.

The fibers can be fabricated such that they include an agent or no agent. Examples of agents can include a chemoattractant, such as SDF-1, or a cell survival promoting factor, such as IGF-1. In one embodiment, SDF-1 may be incorporated within the electrospun fibers and the resultant agent infused electrospun fibers may be dispersed throughout one component of a two-component gel. When delivered, the release of SDF-1 may recruit endogenous stem cells to the infarct region where they will adhere to the electrospun fibers and differentiate into stem cells.

In another embodiment, IGF-1 may be incorporated within the electrospun fibers and the resultant agent infused electrospun fibers may be dispersed throughout one component of a two-component gel. Stem cells may be incorporated within the other component of the two-component gel. When delivered, the stem cells may be temporally immobilized in the gel and adhere to the electrospun fibers. IGF-1 may enhance stem cell survival.

It should be appreciated that any of the above-described methods may be combined to treat an infarct region.

Methods of Treatment

Devices which can be used to deliver each component of the gel include, but are not limited to, dual-needle left-ventricle injection devices and dual-needle transvascular wall injection. Methods of access to use the injection devices include access via the femoral artery or the sub-xiphoid. "Xiphoid" or "xiphoid process" is a pointed cartilage attached to the lower end of the breastbone or sternum, the smallest and lowest division of the sternum. Both methods are known by those skilled in the art.

Figure 5A:
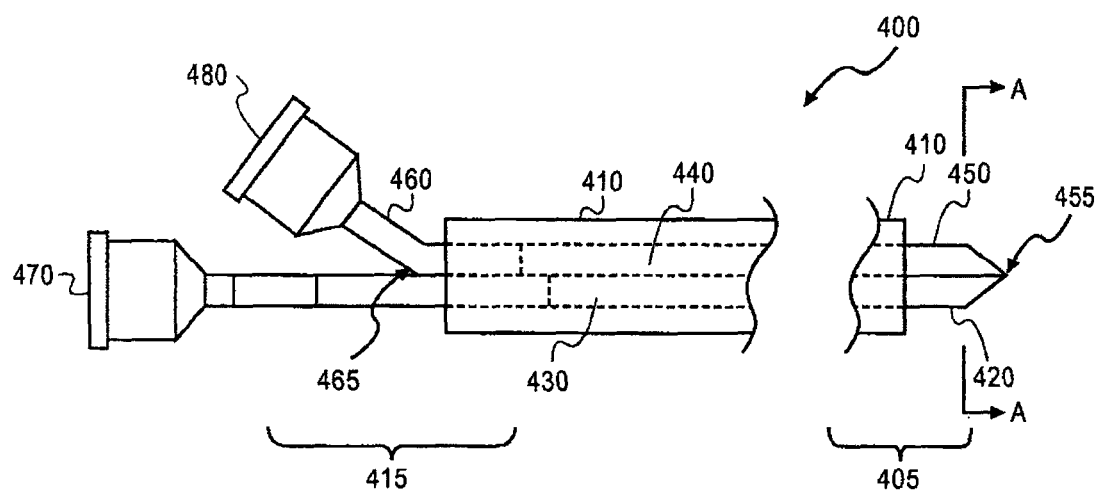
FIGS. 5A-5B illustrate an embodiment of a dual-needle injection device which can be used to deliver the compositions of the present invention.
Figure 5B:
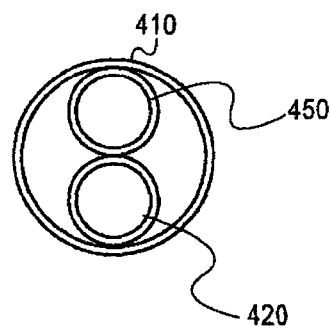

FIGS. 5A-5B illustrate an embodiment of a dual-needle injection device which can be used to deliver the compositions of the present invention. Delivery assembly 400 includes lumen 410 which may house delivery lumens, guidewire lumens and/or other lumens. Lumen 410, in this example, extends between distal portion 405 and proximal end 415 of delivery assembly 400.

In one embodiment, delivery assembly 400 includes main needle 420 disposed within delivery lumen 430. Main needle 420 is movably disposed within delivery lumen 430. Main needle 420 is, for example, a stainless steel hypotube that extends a length of the delivery assembly. Main needle 420 includes a lumen with an inside diameter of, for example, 0.08 inches (0.20 centimeters). In one example for a retractable needle catheter, main needle 420 has a needle length on the order of 40 inches (1.6 meters) from distal portion 405 to proximal portion 415. Lumen 410 also includes separate, possibly smaller diameter, auxiliary lumen 440 extending, in this example, co-linearly along the length of the catheter (from a distal portion 405 to proximal portion 415). Auxiliary lumen 440 is, for example, a polymer tubing of a suitable material (e.g., polyamides, polyolefins, polyurethanes, etc.). At distal portion 405, auxiliary lumen 440 is terminated to auxiliary needle end 450 co-linearly aligned with a delivery end of needle 420. Auxiliary lumen 440 may be terminated to auxiliary needle end 450 with a radiation-curable adhesive, such as an ultraviolet curable adhesive. Auxiliary needle end 450 is, for example, a stainless steel hypotube that is joined co-linearly to the end of main needle 420 by, for example, solder (illustrated as joint 455). Auxiliary needle end 450 has a length on the order of about 0.08 inches (0.20 centimeters). FIG. 5B shows a cross-sectional front view through line A-A' of delivery assembly 400. FIG. 5B shows main needle 420 and auxiliary needle 450 in a co-linear alignment.

Referring to FIG. 5A, at proximal portion 415, auxiliary lumen 440 is terminated to auxiliary side arm 460. Auxiliary side arm 460 includes a portion extending co-linearly with main needle 420. Auxiliary side arm 460 is, for example, a stainless steel hypotube material that may be soldered to main needle 420 (illustrated as joint 465). Auxiliary side arm 460 has a co-linear length on the order of about, in one example, 1.2 inches (3 centimeters).

The proximal end of main needle 420 includes adaptor 470 for accommodating a substance delivery device (e.g., a component of a two-component bioerodable gel material). Adaptor 470 is, for example, a molded female luer housing.

Similarly, a proximal end of auxiliary side arm 460 includes adaptor 480 to accommodate a substance delivery device (e.g., a female luer housing).

The design configuration described above with respect to FIGS. 5A-5B is suitable for introducing two-component gel compositions of the present invention. For example, a gel may be formed by a combination (mixing, contact, etc.) of a first component and a second component. Representatively, a first component may be introduced by a one cubic centimeters syringe at adaptor 470 through main needle 420. At the same time or shortly before or after, second component including treatment agent loaded sustained-release particles may be introduced with a one cubic centimeter syringe at adaptor 480. When the first and second components combine at the exit of delivery assembly 400 (at an infarct region), the materials combine (mix, contact) to form a bioerodable gel.

Figure 6A:
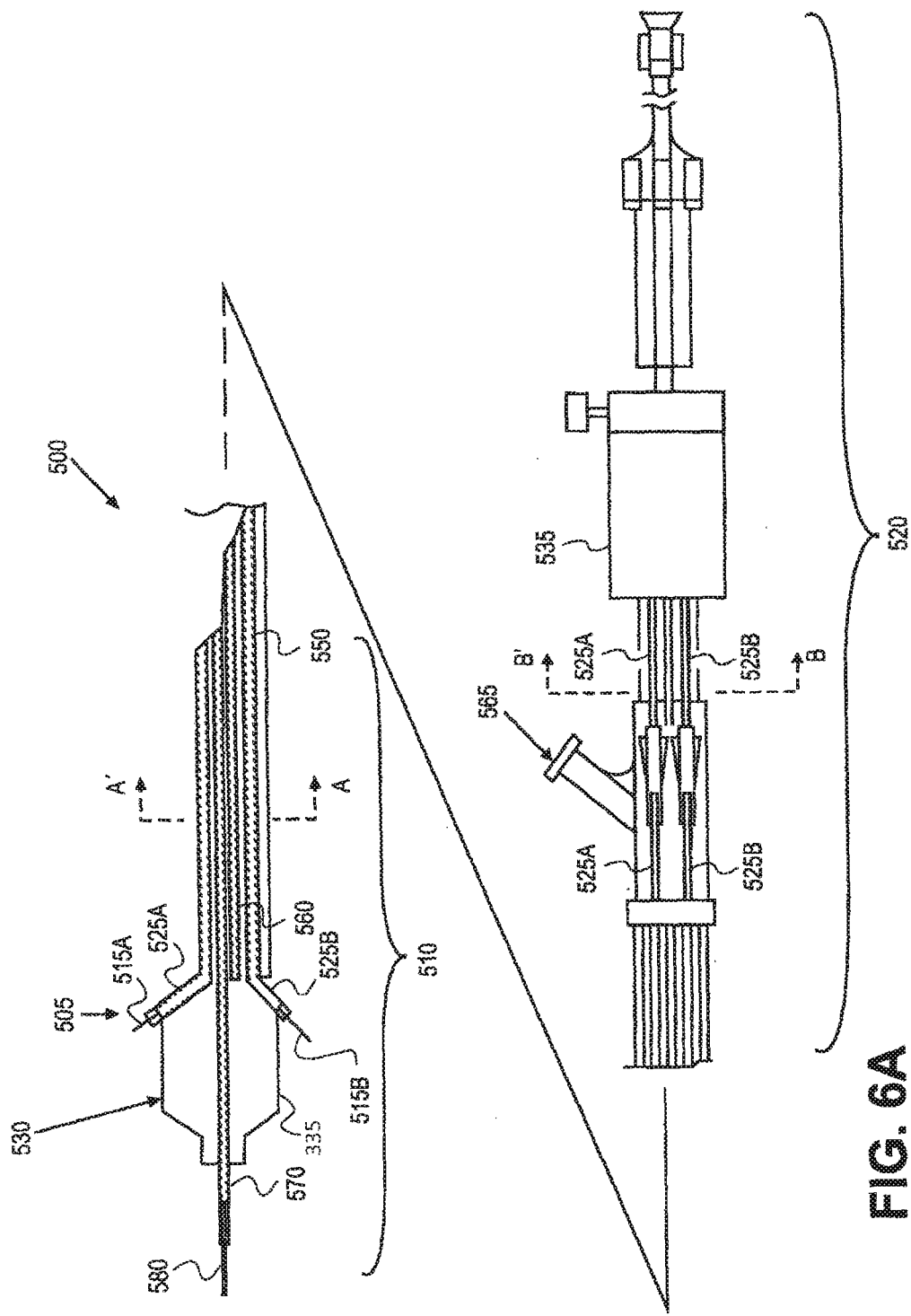
FIGS. 6A-6C illustrate an alternative embodiment of a dual-needle injection device which can be used to deliver the compositions of the present invention.
Figure 6B:
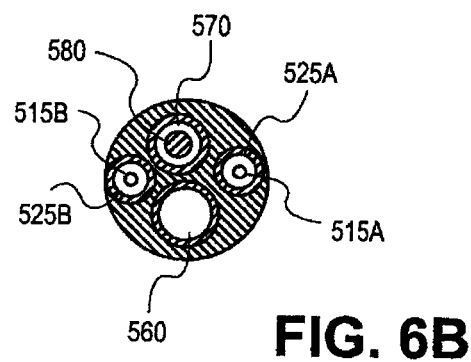
Figure 6C:
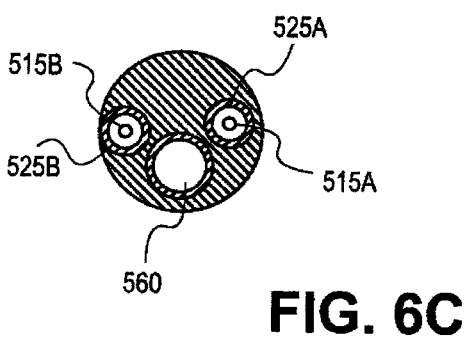

FIGS. 6A-6C illustrate an alternative embodiment of a dual-needle injection device which can be used to deliver two-component gel compositions of the present invention. In general, the catheter assembly 500 provides a system for delivering substances, such as two-component gel compositions, to or through a desired area of a blood vessel (a physiological lumen) or tissue in order to treat a myocardial infarct region. The catheter assembly 500 is similar to the catheter assembly 500 described in commonly-owned, U.S. Pat. No. 6,554,801, titled "Directional Needle Injection Drug Delivery Device", and incorporated herein by reference.

In one embodiment, catheter assembly 500 is defined by elongated catheter body 550 having proximal portion 520 and distal portion 510. FIG. 6B shows catheter assembly 500 through line A-A' of FIG. 6A (at distal portion 510). FIG. 6C shows catheter assembly 500 through line B-B' of FIG. 6A.

Guidewire cannula 570 is formed within catheter body (from proximal portion 510 to distal portion 520) for allowing catheter assembly 500 to be fed and maneuvered over guidewire 580. Balloon 530 is incorporated at distal portion 510 of catheter assembly 500 and is in fluid communication with inflation cannula 560 of catheter assembly 500.

Balloon 530 can be formed from balloon wall or membrane 335 which is selectively inflatable to dilate from a collapsed configuration to a desired and controlled expanded configuration. Balloon 530 can be selectively dilated (inflated) by supplying a fluid into inflation cannula 560 at a predetermined rate of pressure through inflation port 565. Balloon wall 335 is selectively deflatable, after inflation, to return to the collapsed configuration or a deflated profile. Balloon 530 may be dilated (inflated) by the introduction of a liquid into inflation cannula 560. Liquids containing treatment and/or diagnostic agents may also be used to inflate balloon 530. In one embodiment, balloon 530 may be made of a material that is permeable to such treatment and/or diagnostic liquids. To inflate balloon 530, the fluid can be supplied into inflation cannula 560 at a predetermined pressure, for example, between about one and 20 atmospheres. The specific pressure depends on various factors, such as the thickness of balloon wall 335, the material from which balloon wall 335 is made, the type of substance employed and the flow-rate that is desired.

Catheter assembly 500 also includes substance delivery assembly 505 for injecting a substance into a myocardial infarct region. In one embodiment, substance delivery assembly 505 includes needle 515*a* movably disposed within hollow delivery lumen 525*a*. Delivery assembly 505 includes needle 515*b* movably disposed within hollow delivery lumen 525*b*. Delivery lumen 525*a* and delivery lumen 525*b* each extend between distal portion 510 and proximal portion 520. Delivery lumen 525*a* and delivery lumen 525*b* can be made from any suitable material, such as polymers and copolymers of polyamides, polyolefins, polyurethanes and the like. Access to the proximal end of delivery lumen 525*a* or delivery lumen 525*b* for insertion of needle 515*a* or 515*b*, respectively is provided through hub 535. Delivery lumens 525*a* and 525*b* may be used to deliver first and second components of a two-component gel composition to a myocardial infarct region.

Figure 7A:
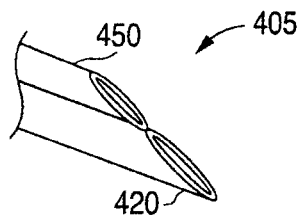
FIGS. 7A-7B illustrate an alternative embodiment of a needle assembly having needles configured side-by-side that can be used to deliver the compositions of the present invention.
Figure 7B:
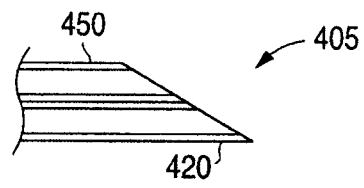

Referring now to FIG. 7A, an alternative embodiment of a distal needle portion 405 is shown. In this embodiment, a proximal edge of the distal end of main needle 420 is near the distal edge of the distal end of auxiliary needle 450. As shown, in this configuration it is possible for the planes encompassing the edges of the distal ends of both needles to be nearly co-planar. This is illustrated further in the cross-sectional view of the needle configuration shown in FIG. 7B. As a result of the nearly co-planar configuration of the distal ends, the distal needle portion 405 can puncture tissue and spread the tissue cleanly as it is advanced further. This minimizes tissue damage and allows the tissue to recover more fully after the distal needle portion 405 is removed.

Figure 8A:
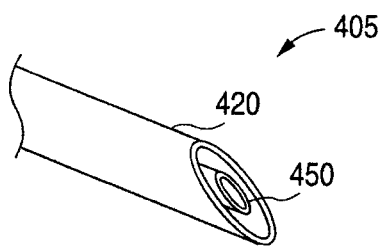
FIGS. 8A-8B illustrate an alternative embodiment of a needle assembly having needles configured generally coaxially that can be used to deliver the compositions of the present invention.
Figure 8B:
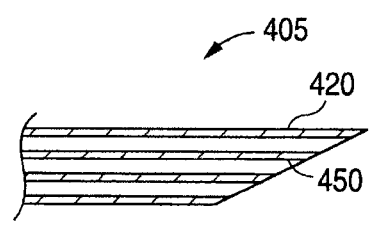

FIG. 8A illustrates yet another alternative embodiment of a distal needle portion 405 in accordance with this invention. In this configuration, the distal portion of auxiliary needle 450 is positioned within the distal portion of main needle 420. The distal ends of the needles may be generally coaxial in order to maximize the flow area of the main needle 420. A sectional view of the needle configuration is shown in FIG. 8B. Although the embodiment is shown in a generally coaxial configuration, the auxiliary needle may also be non-concentric with respect to the main needle. In this way, the flow characteristics of the distal needle portion 405 may be modified in accordance with the invention. This will also account for normal manufacturing tolerances. Further, alternative configurations in accordance with this embodiment can be used to affect the piercing capabilities of the distal needle portion 405.

It is an object of this invention to prevent the inadvertent mixture of the two gel components of the present invention prior to their delivery into the target tissue. Controlling the flow direction of injectate moved through the distal end of each needle will accomplish this. For example, by providing divergent flow paths for each gel component, when the gel components are injected while the distal needle portion is positioned within the turbulent blood flow of a heart chamber, the gel components will be quickly dispersed by the circulating blood before they are able to interact with each other. In contrast, when the distal needle portion 405 is inserted within the heart tissue and the gel components are injected through the divergent flow paths, the resistance of the heart tissue will moderate the dispersal of the gel components, allowing them to admix and form a two-component gel composition.

Figure 9A:
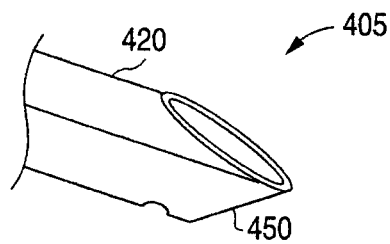
FIGS. 9A-9B illustrate an alternative embodiment of a needle assembly with divergent lumen ports that can be used to deliver the compositions of the present invention.
Figure 9B:
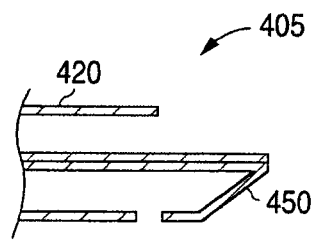

In accordance with this invention, the distal needle portion 405 may be configured as shown in FIGS. 9A-9B. Distal needle portion 405 includes a main needle 420 aligned collinearly with auxiliary needle 450. Main needle 420 includes a lumen opening defined by a plane that intersects the axis of the needle lumen. Thus, a gel component moved through the main needle will exit the needle lumen along the axis of the needle lumen. In contrast, auxiliary needle 450 includes a lumen opening formed in the wall of the needle lumen such that the lumen opening is generally parallel with the needle lumen axis. Thus, a gel component moved through the auxiliary needle will exit the needle lumen in a direction that is generally perpendicular to the needle lumen axis. Therefore a gel component injected through the auxiliary needle 450 exits the distal needle portion 405 in a direction that diverges from the direction that a gel component injected through the main needle 420 will follow as it exits the distal needle portion 405.

As shown in FIG. 9B, the auxiliary needle 450 of this embodiment includes a closed end. The schematic representation of this figure indicates that the end may be closed by forming a needle from one piece with a closed end. Alternatively, an open ended needle tube may be closed by inserting and bonding in place a needle plug. In this case, bonding of the plug may be accomplished by using adhesive or thermal welding, soldering, or any other suitable process that is well known in the art. It may be preferable, though not necessary, to form the plug from the same material as that used to form the auxiliary needle 450, to improve manufacturability.

Figure 10A:
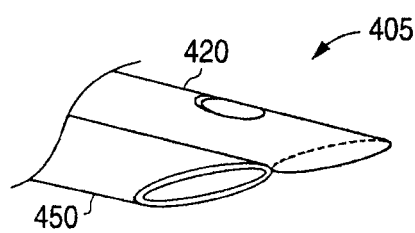
FIGS. 10A-10B illustrate an alternative embodiment of a needle assembly with divergent lumen ports that can be used to deliver the compositions of the present invention.
Figure 10B:
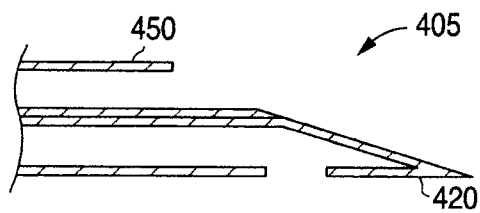

An alternative configuration for a distal needle portion 405 that prevents the inadvertent mixture of injectate is shown in FIGS. 10A-10B. In this embodiment, the lumen openings of main needle 420 and auxiliary needle 450 are not co-planar. Further, in this embodiment, the distal ends of each needle are generally co-planar to each other and the distal edge of a distal end of the auxiliary needle 450 is positioned near the proximal edge of a distal end of the main needle 420. Therefore, a uniform surface is defined by the distal ends of both needles, which improves the piercing characteristics of the needle assembly. In further accordance with the invention, divergent pathways for the gel components are provided to prevent inadvertent mixture outside of the target tissue.

It will be appreciated that the main needle 420 and auxiliary needle 450 of the embodiments shown in FIGS. 7 through 10 are interchangeable. That is, while the main needle 420 of FIG. 10A-10B is shown with a closed end, it is possible to instead close the end of auxiliary needle 450 in accordance with this invention. This interchangeability is applied to each of the embodiments and configurations discussed.

Another method of ensuring that injectate is not inadvertently mixed is to longitudinally space the distal ends of the needles while they are positioned outside of the target tissue. FIG. 11A-11B shows a distal needle portion 405 with a main needle 420 and an auxiliary needle 450 in a longitudinally spaced configuration. In this embodiment, the needles can be moved relative to one another. It will be appreciated that when the distal needle portion 405 is placed within a chamber of a beating heart, the turbulent blood flow within the beating heart will disperse the injectate from each needle before the two components are able to traverse the offset distance 470 to admix. Therefore, inadvertent mixing is prevented.

Referring now to FIG. 11C, when the distal needle portion 405 engages tissue 602, a reactive load is placed on main needle 420 by the tissue 602, causing the main needle 420 to retract relative to auxiliary needle 450 and reducing the offset distance 470. Eventually, both needles engage and puncture the tissue 602. Thus, the subsequent injection of two gel components through the separate needle lumens will result in delivery of the injectate to adjacent locations within the tissue 602, allowing them to effectively mix to form a two-component gel composition in accordance with this invention.

Figure 12B:
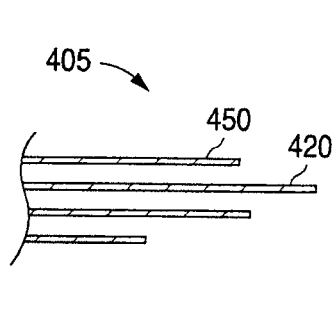
Figure 12C:
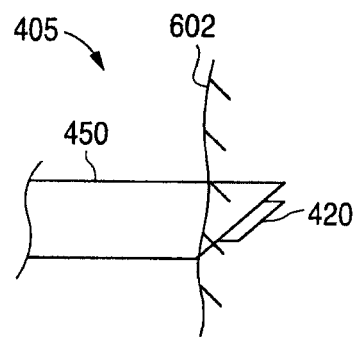

FIGS. 12A-12C illustrates an alternative embodiment in accordance with this invention, using an alternative configuration of distal needle portion 405. In this embodiment, the main needle 420 is at least partially enclosed within the auxiliary needle 450 and the distal end of the main needle is offset from the distal end of the auxiliary needle 450 by a distance 470 when in a first position. In this first position, which is shown in FIG. 12A-12B within the chamber of a heart, gel components delivered through each of the needle lumens will be dispersed by the turbulent blood flow before the two components are able to traverse the offset distance 470 to admix.

Referring now to FIG. 12C, when the distal needle portion 405 engages tissue 602, a reactive load is placed on main needle 420 by the tissue 602, causing the main needle 420 to retract relative to auxiliary needle 450 and reducing offset distance 470. Eventually, both needles engage and puncture the tissue 602. Thus, the subsequent injection of two gel components through the separate needles will result in delivery of the injectate to adjacent locations within the tissue 602, allowing them to effectively mix to form a two-component gel composition in accordance with this invention.

In the embodiments that include an offset distance between needle tips such as those described in FIGS. 11 through 12, it is desirable to ensure that both needle tips pierce the tissue nearly simultaneously. This can be accomplished by constructing the leading needle from a softer material than the other needle. For example, referring to FIG. 12A-12C, if the main needle 420 is fabricated from a polymeric compound such as PEEK, nylon, PEBAX, polyurethane, or another suitable polymer, it will be less likely to pierce the tissue as the catheter is advanced. Instead, it will retract until the auxiliary needle 450 contacts and pierces the tissue, forming a pathway by which the distal needle portion 405 can enter the tissue 602 to deliver the two gel components.

Alternatively, the leading needle may have a blunted distal tip to prevent it from puncturing the tissue before the lagging needle has contacted the tissue also.

Figure 13A:
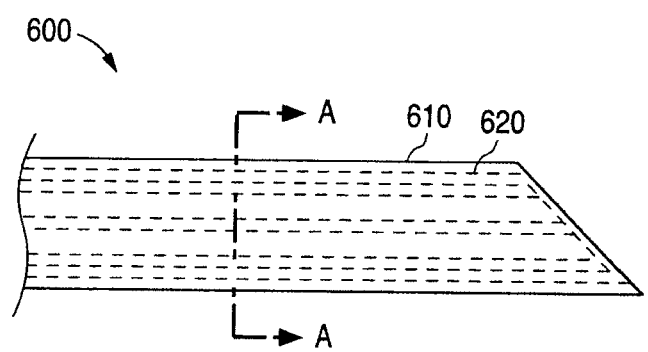
FIGS. 13A-13B illustrate an alternative embodiment of a needle assembly having a guide needle and a delivery needle.

Referring now to FIG. 13A, an alternative embodiment of a needle assembly 600 in accordance with this invention utilizes a guide needle 610 and a delivery needle 620 (hidden). The guide needle 610 is designed to facilitate the puncture of the target tissue, while the delivery needle 620 is intended to deliver the two gel components to the target site. The delivery needle 620 is at least partially positioned within the guide needle 610 and may be moveable within the guide needle. Therefore, the delivery needle may be configured in an initial leading or lagging position relative to the guide needle 610. In accordance with their purpose, the guide needle 610 and the delivery needle 620 may be fabricated from different materials. The guide needle 610 is preferably fabricated from a harder material than the delivery needle 620. Therefore, the guide needle 610 may be formed from a metal such as stainless steel or cobalt chromium, while suitable shape memory metals such as Nitinol may also be used. This provides a guide needle configuration that can puncture tissue easily. The delivery needle 620 may be formed from suitable polymeric compounds such as polyurethane, polyimide, polyamide, PEEK, nylon, Pebax and other suitable plastics that are well known in the art.

Figure 13B:
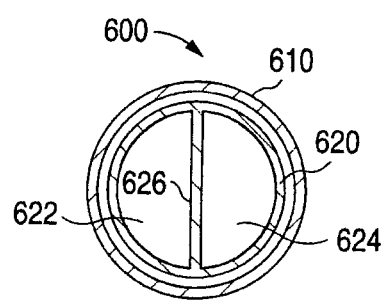

Referring now to FIG. 13B, a cross-sectional view of the needle assembly 600 shown in FIG. 13A is illustrated. This illustrates that the delivery needle 620 includes at least two lumens defined by first lumen 622 and second lumen 624. Further, these lumens may be separated by a partition 626. The main function of the guide needle 610 in this embodiment is to puncture the target tissue thereby forming a channel for the insertion of delivery needle 620. The structure of delivery needle 620 allows different components of a therapeutic composition to be delivered through first lumen 622 and second lumen 624. The components are separated by partition 626 until they exit the distal end of needle assembly 600 and enter the target tissue, where the components admix to form a composition in accordance with this invention.

FIGS. 14A-14C are cross-sectional views of alternative embodiments of delivery needle 620 in accordance with this invention. Each of the variations includes the basic structural components of the delivery needle 620: a first lumen 622, a second lumen 624, and a partition 626. FIG. 14A includes two elliptical lumens 622 and 624 and also exhibits a relatively high amount of material in the sidewall portion that contributes to improved torque transmission. In FIG. 14B, the crescent-shaped second lumen 624 meshes with the circular first lumen 622. The cross-sectional areas of the first lumen 622 and second lumen 624 in this embodiment may be varied to achieve the desired flow rate through each lumen. In FIG. 14C, the delivery needle is generally oval shaped and the first lumen 622 and second lumen 624 are D-shaped. This configuration resists torsion and provides a higher level of flexibility about a first axis 628 compared to the flexibility about a second axis 630. It will be appreciated that many other needle configurations may be contemplated by one skilled in the art that will ensure the separation of injectate during delivery in accordance with this invention.

As discussed in several of the embodiments above, the needle assembly may advantageously comprise a leading needle that is offset from another needle in a first configuration. This prevents mixing of gel components when they are released from the needle assembly outside of the presence of tissue, and therefore mitigates the risk of a thromboembolic event. A suitable offset distance for preventing inadvertent mixture of gel components outside of the target tissue is contemplated to be about 1-5 mm. In a second configuration, the leading needle is moved relative to the lagging needle by a reactive load applied by the target tissue until both needles contact and puncture the tissue. Following tissue puncture, gel components may be delivered through each needle lumen to admix within the target tissue and form a two-component gel composition in accordance with this invention. The two needles may be configured to slide over one another. This can be enabled, for example, by housing the needles within a sheath over at least a portion of their length. Alternatively, the needle components may be constrained within bands placed at predetermined positions along the length of the catheter device.

Referring now to FIG. 15A, a needle assembly 600 is shown in a first configuration prior to making contact with tissue 700. The needle assembly includes a first needle 640 with a distal end that leads the distal end of a second needle 642 in the first configuration. First needle 640 is further associated with first stop 644, while the second needle 642 is associated with a second stop 646. Biasing element 650 is associated with first stop 644 and second stop 646 and applies a separation force to the stops, which biases the distal ends of the first needle 640 and second needle 642 away from each other, as shown.

Referring now to FIG. 15B, as the needle assembly 600 is advanced, the distal end of the leading needle 640 contacts tissue 700 and a reactive load is applied to the first needle 640. This reactive load opposes the biasing force of the biasing element 650 and the first needle 640 moves relative to second needle 642, reducing the offset distance of the distal ends of each needle. When the second needle 642 contacts the tissue 700, the needles puncture the tissue 700. Gel components can then be delivered through first needle 640 and second needle 642 into the tissue in order to form a gel composition therein.

Upon retraction of the needle assembly 600 from the tissue, the biasing element 650 will again force the separation of the distal ends of needle 640 and 642, thereby preventing gelation of the two gel components within the heart chamber and mitigating the risk of a thromboembolic event.

In this embodiment, the stops 644 and 646 may be formed from collars that are bonded to the surface of the needles as described. Bonding may be facilitated through the use of adhesive or thermal welding. Alternatively, the collars may be press fit with the corresponding needle components. The collars are sized and configured to provide adequate seating for the biasing element 650 without excessively impeding the flow of fluid within the needle components.

It may be desirable to vary the distance of the offset between the first and second needle. In this case, an adjustable stop may be provided to on one or both needles to affect this offset distance. The stop may be threaded, for example, and be engaged with a screw thread on the corresponding needle surface. Rotation of the needle via an association with a proximal handle component of the delivery device (not shown) would cause movement of the stop, which would in turn adjust the offset distance between the distal ends of the needle components.

Biasing element 650 is preferably formed from a compression spring that applies a separation load to first needle 640 and second needle 642. However, alternative embodiments are possible, such as the use of a volute, Belleville, tension, v-spring and leaf-type spring, or other configurations that may be contemplated by one skilled in the art.

Ideally, a needle assembly for delivering injectate into tissue will have a minimized cutting profile to reduce tissue damage caused by needle puncture. The ideal needle assembly will also prevent excessive back pressure in order to ease delivery of the injectate. These are competing goals since needle profile can be decreased to minimize puncture size while lumen profile can be increased to reduce back pressure.

Figure 16A:
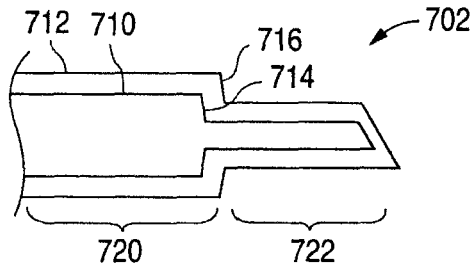
FIGS. 16A-16C illustrate an alternative embodiment of needle assemblies configured to provide beneficial delivery characteristics.
Figure 16B:
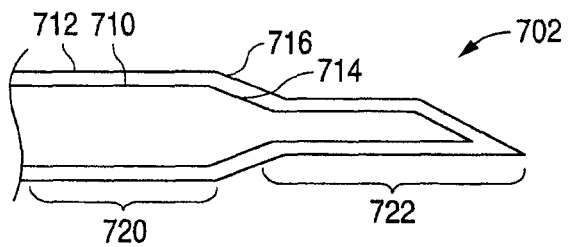
Figure 16C:
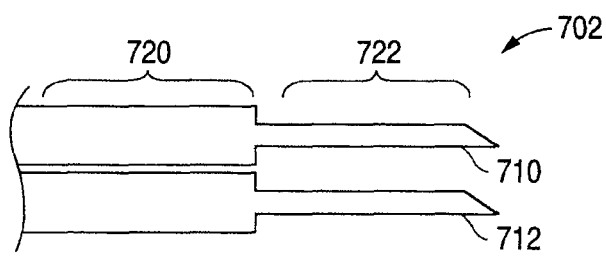

Referring now to FIG. 16A-16C, several embodiments of a needle assembly that minimize puncture area and reduce back pressure are shown. The embodiments generally include a tapered or stepped transition near the distal end of the needle.

FIG. 16A shows a needle assembly 702 comprised of a first needle 710 and a second needle 712. Each needle includes a proximal portion 720 and a distal portion 722, these two portions being separated by a stepped transition zone 714 in the first needle and a stepped transition zone 716 in the second needle. It will be appreciated that the distal portion 722 has a reduced needle profile, which will minimize the cutting profile as it pierces into tissue. In contrast, the proximal portion 720 has a larger lumen profile, which reduces back pressure and eases delivery of an injectate through the needle assembly 702.

Referring now to FIG. 16B, a needle assembly 702 in accordance with this invention is shown in which a distal portion 722 and a proximal portion 720 are separated by a tapered transition zone 714 in a first needle 710 and a tapered transition zone 716 in a second needle 712. This configuration provides the benefit of a needle assembly that minimizes the cutting profile as it pierces tissue and reduces back pressure to ease delivery of injectate through the needle assembly 702.

Referring now to FIG. 16C, an alternative embodiment of a needle assembly 702 in accordance with this invention is shown in which a distal portion 722 and a proximal portion 720 are separated by a stepped transition in first needle 710 and second needle 712. This configuration provides a needle assembly 702 that advantageously minimizes the cutting profile as it pierces tissue and reduces back pressure to ease delivery of injectate through the needle assembly 702. First needle 710 and second needle 712 are arranged in a side-by-side configuration, which optimizes the internal volume in each needle and further contributes to a reduction in back pressure in accordance with this invention.

Figure 17:
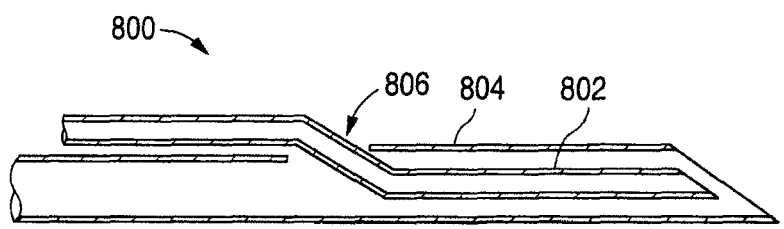
FIG. 17 illustrates an alternative embodiment of a needle assembly that can be used to deliver the compositions of the present invention.

An alternative embodiment of a needle assembly 800 in accordance with this invention is shown in FIG. 17. In this embodiment, a first needle 802 and a second needle 804 are configured in a side-by-side fashion over a portion of their length and they are configured in a generally coaxial fashion over another portion of their length. The needles transition from one configuration to another configuration at a transition point 806 located at a discontinuity in the wall of the second needle 804. The first needle 802 may optionally be sealed to the second needle 804 at the transition point 806. It will be appreciated that this configuration creates a minimized needle profile in the distal portion of the needle assembly 800, while lumen profile may be optimized in the proximal portion of the needle assembly 800, in accordance with this invention.

Figure 18:
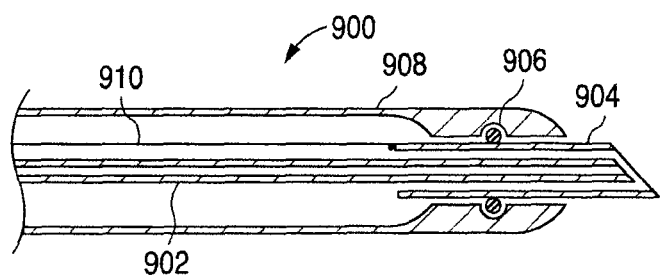
FIG. 18 illustrates an alternative embodiment of a distal portion of an injection device with a needle assembly that can be used to deliver the compositions of the present invention.

Referring now to FIG. 18, yet another embodiment in accordance with this invention is shown. An injection catheter 900 includes a needle assembly that comprises a first needle 902 disposed within a second needle 904, the second needle 904 of this embodiment is shorter than the first needle 902. The second needle 904 is associated with an intermediate catheter shaft 908 by a dynamic seal 906. This seal opposes fluid flow from within the catheter shaft so that fluid exits the injection catheter through second needle 904. Likewise, injectate may be delivered through the lumen of the first needle 902. An actuation element 910 is associated with the second needle 904 near a proximal end of the second needle 904. The actuation element 910 transmits loads to the second needle 904 that cause the needle to either extend or retract. Therefore, the distance between the distal ends of both needles can be controlled by the manipulation of the actuation element 910. In this way, the puncturing of tissue and the creation of a composition therein can be controlled. Further, this configuration provides beneficial reduction in back pressure since the lumen of the catheter shaft is larger than the lumen of second needle 904.

Notwithstanding the description above, the needle components of this invention may be formed from any material that is suitable for the intended purpose. Needle components may therefore be formed from an appropriate metal, such as stainless steel, Nitinol, or cobalt-chromium alloys such as L605 or MP35N, any equivalents thereof, alloys thereof, and combinations thereof. Further, the one or both needle components may be formed from a suitable polymeric compound such as nylon, urethane, polyurethane, polyvinylchloride, polyester, PEEK, PTFE, PVDF, Kyner, polyimide, or polyethylene of various suitable densities. Further, one or both needle components may be a combination of metal and polymer materials, such as a polymer tube reinforced by a metal braid or coil, as are well known in the art.

The needle components described above are sized and configured to puncture the target tissue and effectively deliver the intended gel components therein. Accordingly, a wide range of needle sizes exist for achieving the goal of the invention. Nonetheless, it is contemplated that needle components in accordance with this invention may have an outer dimension at the distal end of between 23 and 33 Gauge.

In accordance with this invention, the bevel angle of the needles may be varied to facilitate tissue puncture. Therefore, the bevel angle could be in the range of 5 to 80 degrees. More preferably, the bevel angle could be in the range of 10 to 65 degrees, and even more preferably, the bevel angle could be in the range of 15 to 45 degrees. Further, it may only be necessary for one of the needle components to include a beveled tip. The beveled tip needle would facilitate tissue puncture, while the second needle may have a blunted or flat tip that is inserted within the punctured tissue.

From the foregoing detailed description, it will be evident that there are a number of changes, adaptations and modifications of the present invention which come within the province of those skilled in the part. The scope of the invention includes any combination of the elements from the different species and embodiments disclosed herein, as well as subassemblies, assemblies and methods thereof. However, it is intended that all such variations not departing from the spirit of the invention be considered as within the scope thereof.

What is claimed is:

1. A needle catheter device comprising:
   an inner delivery needle including a first distal end configured to puncture tissue, wherein the inner delivery needle is hollow and includes a first inlet for delivering a first gel component through the inner delivery needle;
   an outer delivery needle including a second distal end configured to puncture tissue, wherein the outer delivery needle is hollow and includes a second inlet for delivering a second gel component through the outer delivery needle, wherein the first distal end leads the second distal end by a greater offset distance in a first configuration than in a second configuration such that the delivered gel components admix in the second configuration but not in the first configuration; and
   a biasing element associated with the inner delivery needle and the outer delivery needle, wherein the biasing element stores more energy in the second configuration than in the first configuration.

2. The needle catheter device of claim 1, further comprising:
   a first adaptor coupled to the first inlet for delivering the first gel component through the inner delivery needle; and
   a second adaptor coupled to the second inlet for delivering the second gel component through the outer delivery needle, wherein the delivered gel components admix in the second configuration but not in the first configuration.

3. The needle catheter device of claim 2, further comprising:
   a distal portion including the first distal end, the second distal end, and the biasing element;
   a proximal portion including the first adaptor and the second adaptor; and
   an elongated catheter body coupled between the distal portion and the proximal portion.

4. The needle catheter device of claim 1, wherein the biasing element urges the distal ends away from each other in the first configuration.

5. The needle catheter device of claim 4, wherein the first distal end moves relative to the second distal end from the first configuration to the second configuration in response to pressing against tissue.

6. The needle catheter device of claim 4, wherein the offset distance is between 1 to 5 mm in the first configuration.

7. The needle catheter device of claim 1, wherein the inner delivery needle is at least partially enclosed within the outer delivery needle.

8. The needle catheter device of claim 1, wherein the biasing element is a spring selected from the group consisting of compression, tension, volute, Belleville, v-spring, and leaf-type springs.

9. A needle catheter device comprising:
a distal portion including
an inner delivery needle having a first distal end, wherein the inner delivery needle is hollow and includes a first inlet for delivering a first gel component through the inner delivery needle,
an outer delivery needle having a second distal end, wherein the outer delivery needle is hollow and includes a second inlet for delivering a second gel component through the outer delivery needle, and
a biasing element associated with the inner delivery needle and the outer delivery needle at the distal ends;
a proximal portion including
a first adaptor coupled to the first inlet for delivering the first gel component through the inner delivery needle, and
a second adaptor coupled to the second inlet for delivering the second gel component through the outer delivery needle, wherein the first distal end leads the second distal end by a greater offset distance in a first configuration than in a second configuration such that the delivered gel components admix in the second configuration but not in the first configuration; and
an elongated catheter body coupled between the distal portion and the proximal portion.

10. The needle catheter device of claim 9, wherein the biasing element urges the distal ends away from each other in the first configuration.

11. The needle catheter device of claim 10, wherein the first distal end moves relative to the second distal end from the first configuration to the second configuration in response to pressing against tissue.

12. The needle catheter device of claim 10, wherein the offset distance is between 1 to 5 mm in the first configuration.

13. The needle catheter device of claim 9, wherein the first delivery needle is at least partially enclosed within the second delivery needle.

14. The needle catheter device of claim 9, wherein the biasing element is a spring selected from the group consisting of compression, tension, volute, Belleville, v-spring, and leaf-type springs.

15. A method comprising:
advancing a needle catheter device toward a target tissue, the needle catheter device including
an inner delivery needle having a first distal end configured to puncture tissue, wherein the inner delivery needle is hollow and includes a first inlet for delivering a first gel component through the inner delivery needle,
an outer delivery needle having a second distal end configured to puncture tissue, wherein the outer delivery needle is hollow and includes a second inlet for delivering a second gel component through the outer delivery needle, and wherein the first distal end leads the second distal end by an offset distance in a first configuration and in a second configuration, and
a biasing element associated with the inner delivery needle and the outer delivery needle, wherein the biasing element stores more energy in the second configuration than in the first configuration;
contacting, in the first configuration, the target tissue with the first distal end without contacting the target tissue with the second distal end;
moving the first distal end relative to the second distal end from the first configuration to the second configuration until the second distal end contacts the target tissue, wherein the moving decreases the offset distance such that the delivered gel components admix in the second configuration but not in the first configuration, and wherein the moving increases energy stored in the biasing element; and
puncturing, in the second configuration, the target tissue with the first distal end and the second distal end.

16. The method of claim 15, further comprising:
delivering the first gel component through the inner delivery needle and the second gel component through the outer delivery needle, wherein the delivered gel components admix after, but not before, puncturing the target tissue.

17. The method of claim 16, further comprising:
removing the first distal end and the second distal end from the target tissue, wherein the removing increases the offset distance and decreases energy stored in the biasing element.

18. The method of claim 16, wherein the needle catheter device further includes:
a distal portion including the first distal end, the second distal end, and the biasing element;
a proximal portion including a first adaptor coupled to the first inlet for delivering the first gel component through the first delivery needle and a second adaptor coupled to the second inlet for delivering the second gel component through the second delivery needle; and
an elongated catheter body coupled between the distal portion and the proximal portion.

* * * * *